(12) United States Patent
Arndt et al.

(10) Patent No.: US 10,442,863 B2
(45) Date of Patent: Oct. 15, 2019

(54) CONSTRUCT FOR THE DELIVERY OF A MOLECULE INTO THE CYTOPLASM OF A CELL

(71) Applicant: LUTANA GMBH, Stuttgart (DE)

(72) Inventors: Michaela Arndt, Mannheim (DE); Jürgen Krauss, Mannheim (DE); Stefan Kiesgen, Orsfeld (DE)

(73) Assignee: Lutana GMBH, Stuttgart (DE)

( * ) Notice: Subject to any disclaimer, the term of this patent is extended or adjusted under 35 U.S.C. 154(b) by 0 days.

(21) Appl. No.: 15/509,018

(22) PCT Filed: Sep. 7, 2015

(86) PCT No.: PCT/EP2015/070399
§ 371 (c)(1),
(2) Date: Mar. 6, 2017

(87) PCT Pub. No.: WO2016/037985
PCT Pub. Date: Mar. 17, 2016

(65) Prior Publication Data
US 2017/0260274 A1    Sep. 14, 2017

(30) Foreign Application Priority Data
Sep. 8, 2014    (EP) .................................... 14183990

(51) Int. Cl.
*C07K 1/00*    (2006.01)
*C07K 16/28*    (2006.01)
(Continued)

(52) U.S. Cl.
CPC ........ *C07K 16/2863* (2013.01); *A61K 38/465* (2013.01); *A61K 47/65* (2017.08);
(Continued)

(58) Field of Classification Search
None
See application file for complete search history.

(56) References Cited

U.S. PATENT DOCUMENTS 9,296,790 B2 *    3/2016    Chatterjee .............. C07K 14/00

FOREIGN PATENT DOCUMENTS

| JP | 2007527205 A | 9/2007 |
| JP | 2008541768 A | 11/2008 |

(Continued)

OTHER PUBLICATIONS

Seligman, SJ. Constancy and diversity in the flavivirus fusion peptide. Virology Journal. 2008 5:27 (Year: 2008).*

(Continued)

*Primary Examiner* — Michelle S Horning
(74) *Attorney, Agent, or Firm* — Michele M. Wales; Inhouse Patent Counsel, LLC

(57) ABSTRACT

Described is a construct comprising (a) a targeting moiety; (b) a fusogenic moiety consisting one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a molecule which is to be delivered into the cytoplasm of a cell. Moreover, described is a pharmaceutical composition comprising the construct according to the invention and optionally a pharmaceutical acceptable carrier. Further, described is a kit comprising one or more fusogenic sequence(s) derived from dengue virus glycoprotein E comprising the sequence as shown in SEQ ID NO:1 or a sequence which shows 1 to 8 substitutions, deletions, or insertions in comparison to SEQ ID NO:1. Further, described is the use of one or more fusogenic sequence(s) derived from dengue virus glycoprotein E for use in delivery (Continued)

Figure 2:
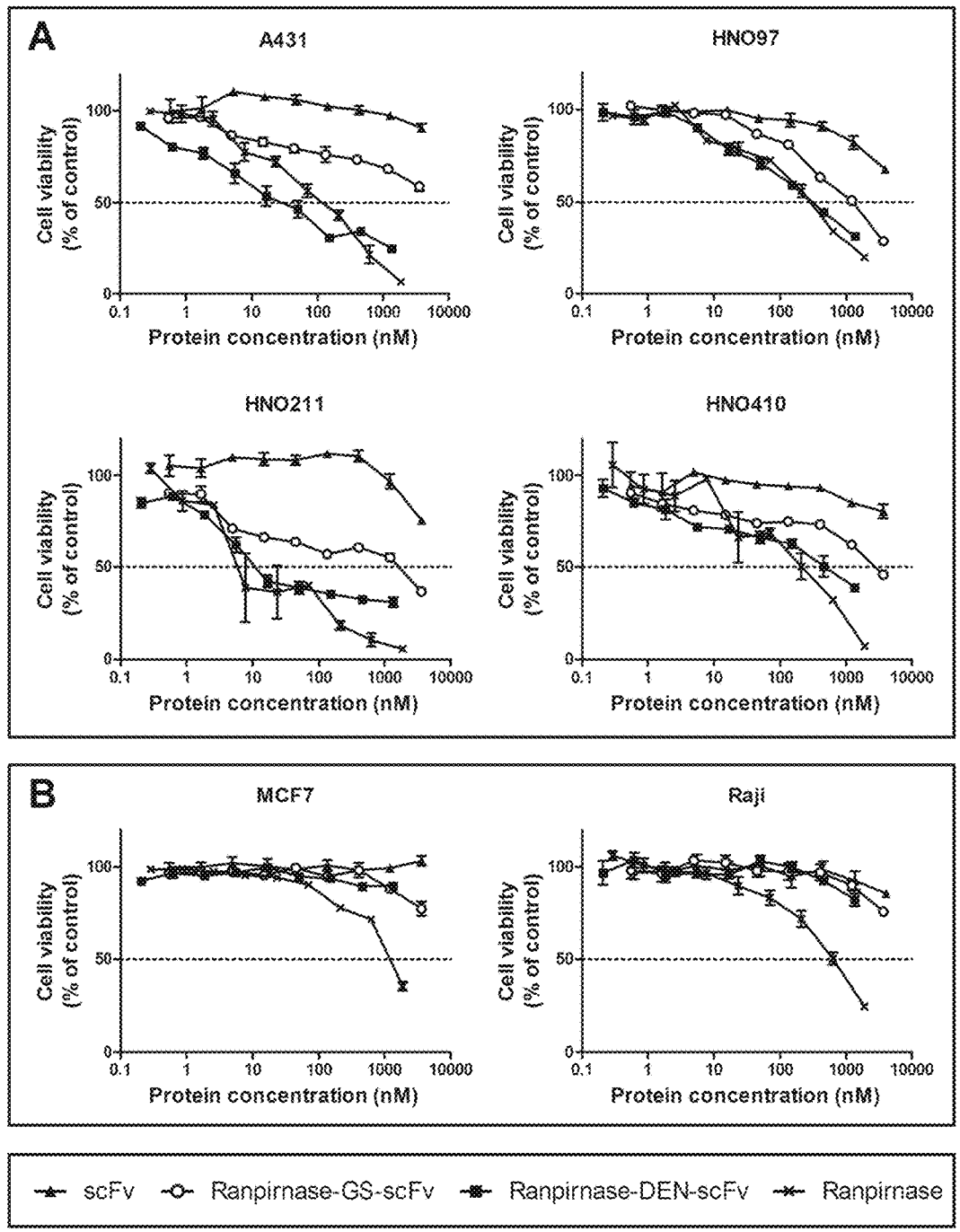

A  N–[ $V_H$ | $(G_4S)_3$ | $V_L$ | c-myc | $His_6$ ]–C

B  N–[ Ranpirnase | $(G_4S)_3$ | $V_H$ | $(G_4S)_3$ | $V_L$ | c-myc | $His_6$ ]–C C  N–[ Ranpirnase | DEN | $V_H$ | $(G_4S)_3$ | $V_L$ | c-myc | $His_6$ ]–C
                      ⎨―――⎬
                MVDRGWGNGCGLFGKGGIV of a therapeutic moiety, a detectable moiety, a nucleic acid molecule, preferably an siRNA, a carrier molecule, preferably a nanoparticle, a liposome and a viral vector into the cytoplasm of a cell.

19 Claims, 3 Drawing Sheets

Specification includes a Sequence Listing.

(51) Int. Cl.
| | |
|---|---|
| *C07K 14/08* | (2006.01) |
| *C07K 16/30* | (2006.01) |
| *A61K 38/46* | (2006.01) |
| *C07K 7/08* | (2006.01) |
| *C12N 7/00* | (2006.01) |
| *C12N 9/22* | (2006.01) |
| *A61K 47/65* | (2017.01) |
| *A61K 47/68* | (2017.01) |
| *A61K 39/00* | (2006.01) |

(52) U.S. Cl.
CPC ............ *A61K 47/6889* (2017.08); *C07K 7/08* (2013.01); *C07K 14/08* (2013.01); *C07K 16/30* (2013.01); *C12N 7/00* (2013.01); *C12N 9/22* (2013.01); *C12Y 301/27* (2013.01); *A61K 2039/505* (2013.01); *A61K 2039/572* (2013.01); *C07K 2317/24* (2013.01); *C07K 2317/622* (2013.01); *C07K 2317/73* (2013.01); *C07K 2317/92* (2013.01); *C07K 2319/10* (2013.01); *C07K 2319/21* (2013.01); *C07K 2319/33* (2013.01); *C07K 2319/41* (2013.01); *C12N 2770/24122* (2013.01); *C12N 2770/24132* (2013.01); *Y02A 50/386* (2018.01)

(56) References Cited

FOREIGN PATENT DOCUMENTS

| | | | |
|---|---|---|---|
| WO | 2004044220 | A2 | 5/2004 |
| WO | 2004078986 | A1 | 9/2004 |
| WO | 2006130855 | A2 | 12/2006 |
| WO | 2009024534 | A2 | 2/2009 |
| WO | 2010040023 | A2 | 4/2010 |
| WO | 2011026026 | A1 | 3/2011 |

OTHER PUBLICATIONS

Kiesgen et al. A fusogenic dengue virus-derived peptide enhances antitumor efficacy of an antibody-ribonuclease fusion protein targeting the EGF receptor. Protein Eng Des Sel. Oct. 2014;27(10):331-7 (Year: 2014).*
Baker et al., Protein Structure Predication and Structural Genomics, Science (2001) vol. 294, No. 5540, pp. 93-96 (Year: 2001).*
Attwood, T. The Babel of Bioinformatics, Science (2000) vol. 290, No. 5491, pp. 471-473 (Year: 2000).*
International Preliminary Report on Patentability dated Mar. 23, 2017 and received in PCT/EP2015/070399.
European Search Report dated Mar. 10, 2015, received in EP141839902.
Hu et al., "Characterization of Retrovirus-Based Reporter Viruses Pseudotyped with the Precursor Membrane and Envelope Glycoproteins of Four Serotypes of Dengue Viruses", Virology, vol. 368, No. 2, pp. 376-387, (2007).
International Search Report and Written Opinion dated Dec. 21, 2015 in PCT/EP2015/070399.
Kiesgen et al., "A Fusogeni Dengue Virus-Derived Peptide Enhances Antitumor Efficacy of an Antibody-Ribonuclease Fusion Protein Targeting the EGF Receptor", Protein Engineering, Design & Selection, vol. 27, No. 10, pp. 331-337, (2014).
Modis et al., "A Ligand-Binding Pocket in the Dengue Virus Envelope Glycoprotein", Proceedings of the National Academy of Sciences of the United States of America, vol. 100, No. 12, pp. 6986-6991, (2003).
Pan et. al., "Synthetic Fusion Peptides of Tick-Borne Encephalitis Virus as Models for Membrane Fusion", Biochemistry, vol. 49, No. 2, pp. 287-296, (2010).
Huang et al., "The Dengue Virus Type 2 Envelope Protein Fusion Peptide is Essential for Membrane Fusion", Virology, vol. 396, pp. 305-315 (2010).
Japanese Office Action and English Translation dated Feb. 27, 2017 received in corresponding Japanese Patent Application No. 2017-532207.

* cited by examiner

A N-[V_H|(G_4S)_3|V_L|c-myc|His_6]-C

B N-[Ranpirnase|(G_4S)_3|V_H|(G_4S)_3|V_L|c-myc|His_6]-C

C N-[Ranpirnase|DEN|V_H|(G_4S)_3|V_L|c-myc|His_6]-C
          MVDRGWGNGCGLFGKGGIV

Figure 1

Figure 3

SEQUENCE LISTING

```
<160> NUMBER OF SEQ ID NOS: 26

<210> SEQ ID NO 1
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 1

Asp Arg Gly Trp Gly Asn Gly Cys Gly Leu Phe Gly Lys Gly Gly Ile
1               5                   10                  15

<210> SEQ ID NO 2
<211> LENGTH: 242
<212> TYPE: PRT
<213> ORGANISM: Artificial Sequence
<220> FEATURE:
<223> OTHER INFORMATION: viral fusogenic sequence

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45
```

```
Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ser Phe
    130                 135                 140

Leu Ser Ala Ser Val Gly Asp Arg Val Thr Ile Thr Cys Arg Ala Ser
145                 150                 155                 160

Gln Ser Ile Gly Thr Asn Ile His Trp Tyr Gln Gln Lys Pro Gly Lys
                165                 170                 175

Ala Pro Lys Leu Leu Ile Lys Tyr Ala Ser Glu Ser Ile Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

Asn Asn Asn Trp Pro Thr Thr Phe Gly Ala Gly Thr Lys Leu Glu Ile
225                 230                 235                 240

Lys Arg

<210> SEQ ID NO 3
<211> LENGTH: 19
<212> TYPE: PRT
<213> ORGANISM: Artificial Sequence
<220> FEATURE:
<223> OTHER INFORMATION: viral fusogenic sequence

<400> SEQUENCE: 3

Met Val Asp Arg Gly Trp Gly Asn Gly Cys Gly Leu Phe Gly Lys Gly
1               5                   10                  15

Gly Ile Val

<210> SEQ ID NO 4
<211> LENGTH: 104
<212> TYPE: PRT
<213> ORGANISM: Rana pipiens
<220> FEATURE:
<221> NAME/KEY: MOD_RES
<222> LOCATION: 1
<223> OTHER INFORMATION: Pyroglutamate

<400> SEQUENCE: 4

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80
```

Lys Ser Thr Asn Lys Phe Cys Val Thr Cys Glu Asn Gln Ala Pro Val
                85                  90                  95

His Phe Val Gly Val Gly Ser Cys
            100

<210> SEQ ID NO 5
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 5

Asp Arg Gly Trp Gly Asn Gly Cys Gly Leu Phe Gly Lys Gly Ser Ile
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 6

Asp Arg Gly Trp Gly Asn Gly Cys Gly Leu Phe Gly Lys Gly Ser Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 7

Asp Arg Gly Trp Gly Asn Gly Cys Gly Leu Phe Gly Lys Gly Gly Val
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 8

Asp Arg Gly Trp His Asn Gly Cys Gly Leu Phe Gly Lys Gly Ser Ile
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 9

Asp Arg Gly Trp His Asn Gly Cys Gly Phe Phe Gly Lys Gly Ser Ile
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 10

Asp Arg Gly Trp Gly Asn Gly Cys Gly Leu Phe Gly Lys Gly Ser Met
1 5 10 15

<210> SEQ ID NO 11
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 11

Asp Arg Gly Trp Gly Asn Gly Cys Gly Leu Phe Gly Lys Gly Ser Tyr
1 5 10 15

<210> SEQ ID NO 12
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 12

Asp Arg Gly Trp Asn Asn Gly Cys Gly Leu Phe Gly Lys Gly Ser Leu
1 5 10 15

<210> SEQ ID NO 13
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 13

Asn Arg Gly Trp Asn Asn Gly Cys Gly Leu Phe Gly Lys Gly Asp Ile
1 5 10 15

<210> SEQ ID NO 14
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 14

Asp Arg Gly Trp Gly Asn His Cys Gly Leu Phe Gly Lys Gly Ser Ile
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 15

Asp Arg Gly Trp Gly Asn Asn Cys Gly Leu Phe Gly Lys Gly Ser Ile
1 5 10 15

<210> SEQ ID NO 16
<211> LENGTH: 16
<212> TYPE: PRT
<213> ORGANISM: Artificial Sequence
<220> FEATURE:
<223> OTHER INFORMATION: viral fusogenic sequence

```
<400> SEQUENCE: 16

Asp Arg Gly Trp Gly Asn Gly Cys Ala Leu Phe Gly Lys Gly Ser Ile
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 17

Asp Arg Gly Trp Gly Asn His Cys Gly Phe Phe Gly Lys Gly Ser Ile
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 18

Asp Arg Gly Trp Asp Ser Gly Cys Phe Ile Phe Gly Lys Gly Glu Val
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 19

Asn Arg Gly Trp Gly Thr Gly Cys Phe Lys Trp Gly Ile Gly Phe Val
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: viral fusogenic sequence

<400> SEQUENCE: 20

Asn Arg Gly Trp Gly Thr Gly Cys Phe Glu Trp Gly Leu Gly Gln Val
1               5                   10                  15

<210> SEQ ID NO 21
<211> LENGTH: 495
<212> TYPE: PRT
<213> ORGANISM: Dengue virus
<220> FEATURE:
<223> OTHER INFORMATION: Glycoprotein E Serotype 2

<400> SEQUENCE: 21

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys His Pro Ala Thr Leu Arg Lys Tyr Cys Ile Glu Ala Lys
    50                  55                  60
```

```
Leu Thr Asn Thr Thr Thr Ala Ser Arg Cys Pro Thr Gln Gly Glu Pro
 65                  70                  75                  80

Ser Leu Asn Glu Glu Gln Asp Lys Arg Phe Val Cys Lys His Ser Met
                 85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
            115                 120                 125

Val Val Gln Pro Glu Asn Leu Glu Tyr Thr Ile Val Ile Thr Pro His
            130                 135                 140

Ser Gly Glu Glu Asn Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Glu Pro
    370                 375                 380

Gly Gln Leu Lys Leu Ser Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
            435                 440                 445

Ser Gly Val Ser Trp Thr Met Lys Ile Leu Ile Gly Val Ile Thr
    450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Val Met Val Gln Ala
```

<210> SEQ ID NO 22
<211> LENGTH: 156
<212> TYPE: PRT
<213> ORGANISM: Homo sapiens
<220> FEATURE:
<223> OTHER INFORMATION: Human pancreatic RNase (RNase 1)

<400> SEQUENCE: 22

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr
145                 150                 155

<210> SEQ ID NO 23
<211> LENGTH: 147
<212> TYPE: PRT
<213> ORGANISM: Homo sapiens
<220> FEATURE:
<223> OTHER INFORMATION: Human Angiogenin (RNase 5) P03950

<400> SEQUENCE: 23

Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Arg Gly Leu Thr Ser Pro Cys Lys
50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145

<210> SEQ ID NO 24
<211> LENGTH: 245
<212> TYPE: PRT
<213> ORGANISM: Artificial Sequence
<220> FEATURE:
<223> OTHER INFORMATION: humanized anti-CD22 scFv (SGIII)

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ile Tyr
            20                  25                  30

Asp Met Ser Trp Val Arg Gln Val Pro Gly Lys Gly Leu Glu Trp Val
        35                  40                  45

Ser Tyr Ile Ser Ser Gly Gly Gly Thr Thr Tyr Tyr Pro Asp Thr Val
    50                  55                  60

Lys Gly Arg Phe Thr Ile Ser Arg Asp Asn Ser Arg Asn Thr Leu Asp
65                  70                  75                  80

Leu Gln Met Asn Ser Leu Arg Val Glu Asp Thr Ala Val Tyr Tyr Cys
                85                  90                  95

Ala Arg His Ser Gly Tyr Gly Ser Ser Tyr Gly Val Leu Phe Ala Tyr
            100                 105                 110

Trp Gly Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Ile Ser Asn Tyr Leu Asn Trp Leu Gln Gln Lys
                165                 170                 175

Pro Gly Lys Ala Pro Lys Leu Leu Ile Tyr Tyr Thr Ser Ile Leu His
            180                 185                 190

Ser Gly Val Pro Ser Arg Phe Ser Gly Ser Gly Ser Gly Thr Glu Phe
        195                 200                 205

Thr Leu Thr Ile Ser Ser Leu Gln Pro Glu Asp Phe Ala Thr Tyr Tyr
    210                 215                 220

Cys Gln Gln Gly Asn Thr Leu Pro Trp Thr Phe Gly Gln Gly Thr Lys
225                 230                 235                 240

Leu Glu Ile Lys Arg
                245
```

<210> SEQ ID NO 25
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="ESR-1s fwd"
      /organism="Artificial Sequence"

<400> SEQUENCE: 25
tatagaagtg cagctggttg aaagc                                        25

<210> SEQ ID NO 26

```
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="ESR-2as rev"
      /organism="Artificial Sequence"

<400> SEQUENCE: 26
tataggatcc acgtttaatt tccag                                           25
```

CONSTRUCT FOR THE DELIVERY OF A MOLECULE INTO THE CYTOPLASM OF A CELL

CROSS-REFERENCE TO RELATED APPLICATIONS

This application is a § 371 National Stage Application of PCT/EP2015/070399 filed on Sep. 7, 2015, which claims priority to EP 14183990.2 filed on Sep. 8, 2014. All of these documents are hereby incorporated by reference in their entirety.

The present invention relates to a construct comprising (a) a targeting moiety; (b) a fusogenic moiety consisting of one or more fusogenic sequence(s) derived from dengue virus glycoprotein E comprising the sequence DRG-WGNGCGLFGKGGI (SEQ ID NO:1) or a sequence which shows 1 to 8 substitutions, deletions, or insertions in comparison to SEQ ID NO:1; and (c) a molecule which is to be delivered into the cytoplasm of a cell. Moreover, the present invention relates to a pharmaceutical composition comprising the construct according to the invention and optionally a pharmaceutical acceptable carrier. Further, the present invention relates to a kit comprising one or more fusogenic sequence(s) derived from dengue virus glycoprotein E comprising the sequence as shown in SEQ ID NO:1 or a sequence which shows 1 to 8 substitutions, deletions, or insertions in comparison to SEQ ID NO:1. Further, the invention relates to the use of one or more fusogenic sequence(s) derived from dengue virus glycoprotein E for use in delivery of a therapeutic moiety, a detectable moiety, a nucleic acid molecule, preferably an siRNA, a carrier molecule, preferably a nanoparticle, a liposome and a viral vector into the cytoplasm of a cell.

Over the last decade, members of the ribonuclease A (RNase A) superfamily have emerged as a potential new class of effector compounds for antibody-targeted therapy of cancer (Newton et al., 2001; De Lorenzo et al., 2004; Arndt et al., 2005; Chang et al., 2010; Liu et al., 2014). Ranpirnase (Onconase®), an RNase from the northern leopard frog *Rana pipiens*, has been extensively studied as an antitumoral agent. It evades the human RNase inhibitor (Haigis et al., 2003) and inhibits protein synthesis by degradation of t-RNA (Saxena et al., 2002). In addition, Ranpirnase targets miRNAs and miRNA precursors being dysregulated in cancer and thus specifically interrupts key mechanisms required for malignant cell growth and tumor progression (Goparaju et al., 2011; Qiao et al., 2012). Despite its amphibian origin, Ranpirnase as a single agent has been shown to mediate no appreciable immunogenicity even when repeatedly administered to cancer patients (Mikulski et al., 1993; Mikulski et al., 2002). Previously, it has been shown that a moderate to several thousand fold increase in tumor cell killing can be achieved by targeted delivery of Ranpirnase using either chemical conjugation or genetic fusion with internalizing antibody derivatives (Newton et al., 2001; Chang et al., 2005; Krauss et 2005b; Liu et al., 2014). Ranpirnase is internalized by clathrin-mediated endocytosis and most likely enters the cytosol from recycling endosomes, which makes its intracellular trafficking unique among members of the RNase A superfamily (Rodriguez et al., 2007). Targeted delivery of Ranpirnase via EGFR internalization may result in different intracellular routing with endosomal entrapment and subsequent lysosomal or proteosomal degradation (Sorkin and Goh, 2009). A monomeric Ranpirnase-anti-CD7 scFv fusion protein has been reported to accumulate in endosomal compartments after efficient internalization. As a result, the fusion protein barely showed cytotoxic activity towards CD7-expressing tumor cells, whereas potent cytotoxicity was observed when the immunoRNase was directly introduced in the cytosol by protein transfection (Erickson et al., 2006). Cytotoxicity of this immunoRNase was also maintained if Ranpirnase was coupled to a CD7-specific antibody by disulfide linkage. Reduction of the disulfide bond after internalization has thus enabled Ranpirnase to enter the cytosol and to gain access to substrates (Erickson et al., 2006).

Although many different factors may contribute to the markedly different cytotoxic properties of different immunoRNases it is conceivable that the extent of overcoming endosomal entrapment (Erickson et al., 2006) is one of the decisive factors for RNases to access cytosolic substrates and finally leading to cell death. Entrapment of protein therapeutics in endo-lysosomal compartments has been reported to be a major reason for impairment or even loss of efficacy (Erickson et al., 2006; Pirie et al., 2011).

The development of methods for efficient and specific delivery of targeted therapeutic agents still remains an issue in biological treatments such as protein and gene therapy. The major uptake mechanism of any biological agents, such as DNA, siRNA and proteins, into cells is the endocytic pathway. Cell targeted agents become entrapped in endosomes and are facing degradation by specific enzymes in the lysosome. Thus, a prerequisite for an effective biological based therapy is to facilitate the endosomal escape and ensure cytosolic delivery of the therapeutic.

Different approaches have been evaluated to overcome endosomal accumulation and lysosomal degradation of targeted fusion proteins, e.g. the use of protein transduction domains (Snyder et al., 2005), leakage-inducing molecules (Weng et al., 2012) or light-induced disruption of the endosomal membrane (Weyergang et al., 2011). Among these strategies, viral protein transduction domains have been successfully exploited as molecular carriers for improved cytosolic delivery of protein-based therapeutics (Chignola et al., 1995; Tolstikov et al., 1997; Hetzel et al., 2008). In recent years, protein transduction domains (PTDs) including viral sequences have been successfully used to improve endosomal escape and antitumor activity of ribonuclease or toxin-based immunoagents (Chignola et al., 1995; Hetzel et al., 2008). PTDs can easily be incorporated into fusion proteins by recombinant DNA technology.

Thus, endosomal escape agents from different sources have been investigated by researchers to facilitate endosomal escape of biologics.

Protein and peptide-based agents are the principal groups of endosomal escape agents which are derived from several viral, bacterial, vegetal and human/animal sources (see also the review article of Varkouhi et al., 2011 J Contr. Release). Furthermore, recombinant DNA technology has enabled the production of small and large molecular weight polypeptides with repeating blocks of amino acids with precise compositions, sequences and lengths. In addition, chemical agents and photochemical methods to rupture the endosomal membrane have been applied. Viruses have evolved several elegant mechanisms to overcome entry barriers in host cells and therefore provide excellent examples of efficient membrane crossing and endosomal escape in nature. Small peptide domains of viral proteins have been used as protein transduction domains or cell penetrating peptides in the context with antibody fusion proteins or antibody conjugates. The most widely studied viral sequences acting with membrane fusion are the protein transduction domain TAT from the HIV 1 transcriptional activator protein Tat, a motif from the PreS2-domain of hepatitis-B virus surface antigen (TLM), the HSV-1 structural protein VP22, and different sequences of the HA2 subunit of haemagglutinin (HA) protein of the influenza virus.

However, depending on the PTD used, specificity of the fusion protein may be diminished because cell entry may occur via direct transduction of the PTD (Bachran et al., 2005). As a consequence, off-target cytotoxicity, i.e., non-specific toxicity, is observed (Fuchs et al., 2013).

To avoid these off-target effects, preservation of the target specificity thus is of fundamental importance.

Thus, there is a need to provide improved means and methods for the delivery of molecules into the cytoplasm of a cell, thereby increasing the efficiency of the molecule to be delivered to the cytoplasm.

The present invention surprisingly demonstrates that a fusogenic sequence derived from dengue virus may be used as a new linker connecting the cytotoxic moiety with the antibody moiety. This linker contains the amino acid residues 98-112 of the putative fusion peptide of glycoprotein E being involved in fusion with endosomal membranes thereby enabling the release of the viral nucleocapsid into the cytosol (Melo et al., 2009; Huang et al., 2010; Zaitseva et al., 2010). In the examples of the present invention, this fusogenic peptide has been used to specifically enhance cytotoxicity of Ranpirnase by promoting efficient translocation into the cytosol. By demonstrating that the cytotoxicity of Ranpirnase-DEN-scFv was far superior to Ranpirnase-GS-scFv lacking the fusogenic linker the present invention provides evidence that access of the RNase to cytosolic substrates is a key step for promoting antitumor activity.

The above technical problem is solved by the provision of the embodiments characterized in the claims. Thus, the present invention provides a construct comprising (a) a targeting moiety; (b) a fusogenic moiety consisting of one or more fusogenic sequence(s) derived from dengue virus glycoprotein E comprising the sequence DRG-WGNGCGLFGKGGI (SEQ ID NO:1) or a sequence which shows 1 to 8 substitutions, deletions, or insertions in comparison to SEQ ID NO:1; and (c) a molecule which is to be delivered into the cytoplasm of a cell.

Surprisingly, the present invention demonstrates that the sequence DRGWGNGCGLFGKGGI (SEQ ID NO:1) derived from dengue virus glycoprotein E leads to a significant improvement of the specific cytotoxicity of an immunoRNase comprising a humanized anti-EGFR scFv and Ranpirnase by a factor of up to 95 compared to a construct that lacks the viral sequence while off-target effects (non-specific cytotoxicity) are avoided.

This is in particular surprising since it is unpredictable to isolate a particular sequence from its viral protein's natural context and, artificially, implement it in the context of a construct since one cannot predict whether (i) the respective viral sequence exerts a capability to mediate the "endosomal escape" at all, while, at the same time, off-target effects, i.e., non-specific cytotoxicities are avoided.

Yet, as mentioned above, the technical problem of providing improved means and methods for the delivery of molecules into the cytoplasm of a cell, thereby increasing the efficiency of the molecule to be delivered to the cytoplasm is solved and the present invention provides a construct comprising (a) a targeting moiety; (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a molecule which is to be delivered into the cytoplasm of a cell.

The construct of the present invention preferably comprises three main modules, i.e., a targeting moiety; (b) a fusogenic moiety consisting of one or more fusogenic sequence(s) and (c) a molecule which is to be delivered into the cytoplasm of a cell (i.e., a "cargo"). Yet, it is also envisaged that the construct may also lack one of these three modules. Thus, as will be explained further below, the construct may also lack a molecule which is to be delivered into the cytoplasm of a cell since it is conceivable that the targeting moiety itself represents the "cargo", i.e., the molecule which is to be delivered into the cytoplasm of a cell. Accordingly, in such a case, the construct merely comprises two main modules, i.e., a targeting moiety; and (b) a fusogenic moiety consisting of one or more fusogenic sequence(s).

One module of the construct, i.e., "targeting moiety" relates to a molecule which is capable of specifically delivering an attached molecule to a given cell type and is preferably capable of associating with a given marker, preferably an antigen, which is associated with that cell type. Thus, the "targeting moiety" is capable of specifically detecting and binding to its target, i.e., a given (marker) structure on the surface of a cell which is specifically found with a certain target cell. The present invention is not limited with respect to the "targeting moiety" since the nature of the targeting moiety depends on the desired cell into which cytoplasm the "cargo" is to be delivered. Therefore, further below, only non-limiting examples for the targeting moiety are given. The person skilled in the art is aware of "targeting moieties" (or corresponding antigens) which are specific for a given cell. Specific for a cell means that a certain targeting moiety (or a corresponding antigen) is exclusively, or at least predominantly, present on a given (target) cell while it is not present on other cells.

The second module of the construct, i.e., the fusogenic moiety consisting of the fusogenic sequence(s), is a moiety or a sequence which facilitates the membrane crossing and the endosomal escape and, accordingly, mediates the release of a given molecule from the endosome into the cytoplasm of the cell.

The third module of the construct, i.e., the "cargo" or the molecule which is to be delivered into the cytoplasm of a cell may be any desired molecule which is, e.g., not naturally occurring/present in the cytoplasm of a cell. Thus, any conceivable "cargo" may be used as long as it is desirable to direct this molecule into the cytoplasm of a certain cell. Therefore, the present invention is not limited to a certain "cargo" and, accordingly, only non-limiting examples are provided further below.

The construct may be present in the form of a fusion protein, i.e., a protein which is formed by the expression of a hybrid gene made by combining at least two gene sequences. Typically, as will be explained in more detail further below, this is accomplished by cloning a cDNA into an expression vector in frame with an existing gene. Accordingly, the construct may be a fusion protein, i.e., a chimeric molecule which is formed by joining two or more polypeptides via a peptide bond between the amino terminus of one module and the carboxyl terminus of another molecule. In this way, the above at least two modules, preferably all three modules are joined together in the form of a fusion protein provided that the at least two modules, preferably the three modules, are proteinaceous of nature. Once cloned in frame, the fusion protein is then recombinantly expressed by a corresponding nucleic acid sequence encoding said fusion protein.

Alternatively, the at least two modules, preferably all three modules may also be covalently coupled by a chemical conjugate. Thus, the modules of the construct may be chemically coupled in a covalent linkage.

It is also conceivable that two modules are in the form of a fusion protein while the third module is chemically coupled in a covalent linkage. In particular, in case the "cargo" is of non-proteinaceous nature, it is chemically coupled to module (a) and module (b) via a covalent linkage.

The arrangement of the three modules within the conjugate is not particularly limited. Accordingly, the fusogenic moiety/the fusogenic sequence (b) may be located between the targeting moiety (a) and the molecule (c) which is to be delivered to the cytoplasm (i.e., the "cargo"). However, other positions of the fusogenic moiety/fusogenic sequence(s) of the present invention are possible. Thus, the fusogenic moiety/fusogenic sequence(s) may also be placed at either end (i.e., at the N- or C-terminal end in case of a fusion protein). Thus, the construct may have the arrangement of (b)-(c)-(a) or (b)-(a)-(c) or (c)-(a)-(b) or (c)-(b)-(a). Accordingly, module (c), (a) and (b), respectively, may be located between the other modules (b) and (a), (b) and (c), (c) and (b) and (c) and (a), respectively. Yet, preferably, the fusogenic moiety/fusogenic sequence(s) is located between the targeting moiety (a) and the molecule which is to be delivered in the cytoplasm of a cell (c) and, accordingly, the construct may have the arrangement of (a)-(b)-(c) or (c)-(b)-(a).

The construct may also lack a targeting moiety. Thus, in such a construct, the fusogenic moiety/fusogenic sequence may be directly fused (or chemically coupled in a covalent linkage) to a molecule which is to be delivered into the cytoplasm of a cell. The localization of the fusogenic moiety/fusogenic sequence(s) may be at either end.

As mentioned above, the construct may also lack the "cargo", i.e., the molecule which is to be delivered to the cytoplasm of a cell since the targeting moiety itself may at the same time be the molecule which is to be delivered to the cytoplasm of a cell. Thus, in such a construct, the fusogenic moiety/fusogenic sequence(s) may be directly fused to (or chemically coupled in a covalent linkage) to the targeting moiety. In such a case, the targeting moiety is preferably an antibody or an antigen binding fragment as defined further below. The localization of the fusogenic moiety/fusogenic sequence(s) may be at either end.

The main module of the construct of the present invention is the targeting moiety consisting of one or more fusogenic sequence(s) which is derived from dengue virus glycoprotein E and which comprises the amino acid sequence DRGWGNGCGLFGKGGI (SEQ ID NO:1).

"One or more" means that the targeting moiety may harbor one fusogenic sequence of the present invention. The targeting moiety may also harbor two, three or four fusogenic sequences of the present invention. Alternatively, the targeting moiety may also harbor five or even more fusogenic sequences of the present invention.

The full-length sequence of the dengue virus glycoprotein E serotype 2 is known in the art and has the sequence as shown in SEQ ID NO:21. While in the appended examples, the sequence from amino acids 96 to 114 of the dengue virus glycoprotein E serotype 2 has been used (i.e., the amino acid sequence MVDRGWGNGCGLFGKGGIV (SEQ ID NO:3)) the fusogenic sequence of the present invention at least comprises the core region of amino acids 98 to 113 of the glycoprotein E of the dengue virus glycoprotein E serotype 2, i.e., the amino acid sequence DRGWGNGCGLFGKGGI (SEQ ID NO:1). Yet, preferably, the fusogenic sequence(s) which is derived from dengue virus glycoprotein E comprises the amino acid sequence MVDRGWGNGCGLFGKGGIV (SEQ ID NO:3).

However, the fusogenic sequence(s) as used in the present invention is/are not particularly limited to the above specific sequences but may also be a fusogenic sequence which comprises a sequence which shows 1 to 8 substitutions, deletions, or insertions in comparison to SEQ ID NO:1. Alternatively, the fusogenic sequence may also be a sequence which comprises a sequence which shows 1 to 8 substitutions, deletions, or insertions in comparison to SEQ ID NO:3. The fusogenic sequence may also be a sequence which comprises a sequence which shows 1 to 7 substitutions, deletions, or insertions in comparison to SEQ ID NO:1 (or SEQ ID NO:3). The fusogenic sequence may also be a sequence which comprises a sequence which shows 1 to 6 substitutions, deletions, or insertions in comparison to SEQ ID NO:1 (or SEQ ID NO:3). The fusogenic sequence may also be a sequence which comprises a sequence which shows 1 to 5 substitutions, deletions, or insertions in comparison to SEQ ID NO:1 (or SEQ ID NO:3). The fusogenic sequence may also be a sequence which comprises a sequence which shows 1 to 4 substitutions, deletions, or insertions in comparison to SEQ ID NO:1 (or SEQ ID NO:3). The fusogenic sequence may also be a sequence which comprises a sequence which shows 1 to 3 substitutions, deletions, or insertions in comparison to SEQ ID NO:1 (or SEQ ID NO:3). The fusogenic sequence may also be a sequence which comprises a sequence which shows 1 to 2 substitutions, deletions, or insertions in comparison to SEQ ID NO:1 (or SEQ ID NO:3). Most preferably, the fusogenic sequence may also be a sequence which comprises a sequence which shows 1 substitution, deletion, or insertion in comparison to SEQ ID NO:1 (or SEQ ID NO:3).

Preferably, the position(s) of the above amino acid substitution(s), deletion(s) or insertion(s) in comparison to SEQ ID NO:1 (or SEQ ID NO:3) are performed at (a) position(s) which is/are less conserved in the sequence of SEQ ID NO:1 (or SEQ ID NO:3) in comparison with corresponding sequences dengue virus glycoprotein E sequences of other Flaviviridae family members. The sequence of the present invention is known to be highly conserved among members of the Flaviviridae family.

In order to determine whether a certain amino acid position is less conserved and, therefore, preferably subject to a modification as outlined above, the skilled person can use means and methods well known in the art, e.g. alignments, either manually or by using computer programs known to the person skilled in the art. Such an alignment can, e.g., be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences. Preferably, ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Those positions which turn out to be "identical" (i.e., "conserved" among members of the Flaviviridae family) are preferably not subject to a substitution, deletion or insertion. In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same with SEQ ID NO: 1 or SEQ ID NO:3. Preferably, the described identity exists over a region that is at least about 19 amino acids (i.e., the above-mentioned amino acids 96 to 114 of the dengue virus glycoprotein E serotype 2 (i.e., the amino acid sequence MVDRGWGNGCGLFGKGGIV (SEQ ID NO:3)) or over a region that is at least about 16 amino acids (i.e., the above-mentioned core region of amino acids 98 to 113 of the glycoprotein E of the dengue virus glycoprotein E serotype 2, i.e., the amino acid sequence DRGWGNGCGLFGKGGI (SEQ ID NO:1). Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff (1989) PNAS 89:10915) uses alignments (B) of 50, expectation (E) of 10, M=5, N=4, and a comparison of both strands.

Preferably, the above up to 1, 2, 3, 4, 5, 6, 7, or 8 amino acid substitutions are conservative amino acid substitutions with reference to the sequences of SEQ ID NOs: 1 and 3.

These "conservative amino acid substitution(s)" refer to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson Molecular Biology of the Gene, The Benjamin/Cummings Pub. Co. 4th Ed. (1987), 224. In addition, substitutions of structurally or functionally similar amino acids are less likely to disrupt biological activity. Within the context of the present invention the fusogenic sequence(s) of the present invention comprise polypeptide chains with sequences that include up to 0 (no changes), 1, 2, 3, 4, 5, 6, 7, or 8 conservative amino acid substitutions when compared with the specific amino acid sequences disclosed herein, for example, SEQ ID NO: 1 or SEQ ID NO:3.

Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The fusogenic sequence which has one or more of the above substitutions, deletions or insertions in comparison to SEQ ID NO:1 (or SEQ ID NO:3) may result in a fusogenic sequence having a similar capability (in terms of fusogenic properties) as SEQ ID NO:1 (or SEQ ID NO:3), preferably higher capability as SEQ ID NO:1 (or SEQ ID NO:3). The property/capability of a given modified fusogenic sequence in comparison to SEQ ID NO:1 (or SEQ ID NO:3) can easily be determined by the skilled person by methods known in the art and as outlined in the appended examples. Thus, the (fusogenic) property/capability of a given modified fusogenic sequence in comparison to SEQ ID NO:1 (or SEQ ID NO:3) relates to the activity of a certain respective sequence to have the ability to mediate the "endosomal escape" (i.e., the facilitation of the fusogenic sequence to allow for the membrane crossing and the endosomal escape and, accordingly, the mediation of the release of a given molecule from the endosome into the cytoplasm of the cell) while, at the same time, off-target effects, i.e., non-specific cytotoxicity are avoided/reduced. The "endosomal escape" and the "non-specific cytotoxicity" can, e.g., be determined by methods described in the appended examples and as outlined in the following.

The endosomal escape efficiency of a targeted protein with cytotoxic properties can be determined by a cell viability assay. Using this assay, the concentration of the targeted protein containing a fusogenic sequence (e.g., an immunoRNase fusion protein) which is required to reduce the cell viability by 50% (IC50) can be determined and compared with the IC50 of a targeted control protein lacking a fusogenic sequence. For this, target cells are seeded in a 96-well flat-bottom plate and incubated with different concentrations of the targeted protein or buffer as control at 37° C., 5% $CO_2$ for 72 h in a total volume of 100 μl. Cell viability can be determined, e.g., by the addition of 20 μl of a 5 mg/ml solution of 3-(4,5-dimethylthiazol-2-yl)-2,5-diphenyltetrazolium bromide (MTT) diluted in PBS. After incubation with MTT at 37° C., 5% $CO_2$ for 4 h, the medium is removed and cells are lysed in 100 μl lysis solution (10% SDS (w/v) and 0.6% acetic acid (v/v) in dimethyl sulfoxide) per well. Plates are incubated at room temperature for 5 min followed by gentle agitation for 5 min to dissolve released formazan crystals. Formazan concentration is determined by measuring the absorbance at 570 nm (reference: 620 nm)

using a microplate reader (e.g. Infinite F200Pro Tecan). Alternatively the cell viability can be determined by adding 10 μl alamarBlue® (ThermoScientific, Rockford, Ill., USA) per well and incubation at 37° C., 5% $CO_2$ for 4 h without subsequent cell lysis. Absorbance can be directly measured using the same wavelengths and instrumentation as for MTT-treated cells. Cell viability is expressed as percentage of viable cells treated with targeted protein related to buffer control. Thus, the cell viability determined in the above assay serves as a readout for determining the property/capability of a given fusogenic sequence. A putative fusogenic sequence has a similar capability (in terms of fusogenic properties) as SEQ ID NO:1 (or SEQ ID NO:3), preferably a higher capability as SEQ ID NO:1 (or SEQ ID NO:3) provided that the cell viability is reduced compared to a corresponding control fusion protein lacking the respective (putative) fusogenic sequence.

Non-specific cytotoxicity can be proven by using the above described cell viability assays in the context with non-targeted cells (e.g. antigen-negative cells).

However, the fusogenic sequence(s) as used in the present invention is/are not particularly limited to the above specific sequences and the above described deletions, substitutions or insertions but may also relate to a fusogenic sequence which comprises a sequence which shows (an) amino acid(s) addition(s) in comparison to SEQ ID NO:1 or SEQ ID NO:3. The addition of amino acid(s) can be flanking or interspersed. Thus, the additional amino acids may be added at the N- and/or C-terminal end of the fusogenic sequence(s) of the present invention. Alternatively, or in addition to these flanking additional amino acids, the additional amino acids may also be within the amino acid sequence of the fusogenic sequence(s) of the present invention. The additional amino acid(s) comprise polypeptide chains of up to 0 (no changes), 1, 2, 3, 4, 5, 6, 7, 8, 9 or 10 amino acids, preferably of up to 20 amino acids or even more preferably of up to 30 amino acids. In light of the rationale that the addition of amino acids is likely not to change the above functional properties of the fusogenic sequence of the invention the addition of the amino acids may also have a length of up to 40, 50, 60, 70, 80, 90, or even 100 amino acids or even more, up to 200, 300, 400 or 500 amino acids as long as these sequences have a similar capability (in terms of fusogenic properties) as SEQ ID NO:1 (or SEQ ID NO:3), preferably higher capability as SEQ ID NO:1 (or SEQ ID NO:3) as defined above.

In the construct according to the present invention, the fusogenic sequence may be selected from the group consisting of

DRGWGNGCGLFGKGSI, (SEQ ID NO: 5)

DRGWGNGCGLFGKGSL, (SEQ ID NO: 6)

DRGWGNGCGLFGKGGV, (SEQ ID NO: 7)

DRGWHNGCGLFGKGSI, (SEQ ID NO: 8)

DRGWHNGCFFGKGSI, (SEQ ID NO: 9)

DRGWGNGCGLFGKGSM, (SEQ ID NO: 10)

DRGWGNGCGLFGKGSY, (SEQ ID NO: 11)

DRGWNNGCGLFGKGSL, (SEQ ID NO: 12)

NRGWNNGCGLFGKGDI, (SEQ ID NO: 13)

DRGWGNHCGLFGKGSI, (SEQ ID NO: 14)

DRGWGNNCGLFGKGSI, (SEQ ID NO: 15)

DRGWGNGCALFGKGSI, (SEQ ID NO: 16)

DRGWGNHCGFFGKGSI, (SEQ ID NO: 17)

DRGWDSGCFIFGKGEV, (SEQ ID NO: 18)

NRGWGTGCFKWGIGFV (SEQ ID NO: 19)
and

NRGWGTGCFEWGLGQV. (SEQ ID NO: 20)

However, the fusogenic sequence(s) as used in the present invention is/are not particularly limited to the above specific sequences of SEQ ID NOs:5 to 20 but may also be a fusogenic sequence which comprises a sequence which shows 1 to 8 substitutions, deletions, or insertions in comparison to SEQ ID NOs:5 to 20, respectively. In this respect, as regards the degree of the substitutions, deletions or insertions, the same applies, mutatis mutandis, to SEQ ID NOs: 5 to 20 as has already been set forth above with respect to SEQ ID NO:1 and SEQ ID NO:3. Moreover, the fusogenic sequence(s) are not limited to the above SEQ ID NOs: 5 to 20 but may also relate to fusogenic sequence(s) which comprise a sequence which shows (an) amino acid(s) addition(s) in comparison to said sequences. In this respect, as regards the addition of (an) amino acid(s) the same applies, mutatis mutandis, as has already been set forth above for SEQ ID NO:1 and SEQ ID NO:3.

The fusogenic sequence(s) of the present invention may be recombinantly or synthetically generated/synthesized by methods known to the person skilled in the art. More specifically, as described further below, the fusogenic peptide of the present invention may be produced either recombinantly by methods known to the person skilled in the art or may, e.g., be conveniently synthesized on an automated peptide synthesizer using a solid-phase support and standard techniques of repetitive orthogonal deprotection and coupling. Free amino groups in the peptide, that are to be used later for conjugation of moieties or other agents, are advantageously blocked with standard protecting groups such as a Boc group, while N-terminal residues may be acetylated to increase serum stability. Such protecting groups are well known to the skilled person; see Greene and Wuts Protective Groups in Organic Synthesis, 1999 (John Wiley and Sons, N.Y.). When the peptides are prepared for later use within the construct of the present invention, they are advantageously cleaved from the resins to generate the corresponding C-terminal amides, in order to inhibit in vivo carboxypeptidase activity.

As mentioned above, one module of the construct, i.e., the "targeting moiety", relates to a molecule which is capable of specifically delivering an attached molecule to a given cell type and is preferably capable of associating with a given marker, preferably an antigen, which is associated with that cell type. Thus, the "targeting moiety" is capable of specifically detecting and binding to its target, i.e., a given (marker) structure on the surface of a cell which is specifically found with a certain target cell.

The term "binding to" as used in the context of the present invention defines a binding (interaction) of at least two "antigen-interaction-sites" with each other, i.e., the targeting moiety on the one hand and the corresponding antigen or epitope on the cell surface on the other hand. The term "antigen-interaction-site" defines, in accordance with the present invention, a motif of the targeting moiety, preferably a part of the antibody or antibody fragment or a cytokine or a ligand, which shows the capacity of specific interaction with a specific antigen or a specific group of antigens of the cell which is to be targeted. Said binding/interaction is also understood to define a "specific recognition". The term "specifically recognizing" means in accordance with this invention that the targeting moiety is capable of specifically interacting with and/or binding to at least one surface structure which is specific for the cell which is to be targeted. The targeting moiety can interact and/or bind to (an) epitope(s) on cell which is to be targeted while this structure, antigen or epitope is specific for the cell which is to be targeted. The term "specifically recognizing" relates to the specificity of the targeting moiety, i.e., to its ability to discriminate between the specific regions of a cell which is to be targeted and a cell which is not to be targeted and which, therefore, does not have the structure, antigen or epitope which is specific for the cell which is to be targeted. The skilled person knows and can derive structures, epitopes, surface markers and/or antigens which are specific for a certain cell and which are not present on non-target cells and can easily select the target accordingly. Non-limiting examples are given further below.

The term "specific interaction" as used in accordance with the present invention means that the targeting moiety does not or does not essentially cross-react with (poly) peptides, structures, epitopes, surface markers and/or antigens of similar structures.

Cross-reactivity of a panel of targeting moieties under investigation may be tested, for example, by assessing binding of said panel of targeting moieties under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the structure of interest as well as to a number of more or less (structurally and/or functionally) closely related structures. Only those targeting moieties that bind to the certain chosen structure of a cell which is to be targeted (i.e., a structure which is specific for said cell), but do not or do not essentially bind to any of the other structures, are considered specific for said cell of interest and selected. These methods may comprise, inter alia, binding studies, blocking and competition studies with structurally and/or functionally closely related molecules. These binding studies also comprise FACS analysis, surface plasmon resonance (SPR, e.g. with BIAcore®), analytical ultracentrifugation, isothermal titration calorimetry, fluorescence anisotropy, fluorescence spectroscopy or by radiolabeled ligand binding assays.

The term "binding to" does not only relate to a linear structure, e.g., a linear epitope, but may also relate to a conformational epitope, a structural epitope or a discontinuous epitope consisting of two regions of the human target molecules or parts thereof. In the context of this invention, a conformational epitope is defined by two or more discrete amino acid sequences separated in the primary sequence which comes together on the surface of the molecule when the polypeptide folds to the native protein (Sela, Science 166 (1969), 1365 and Laver, Cell 61 (1990), 553-536). Moreover, the term "binding to" is interchangeably used in the context of the present invention with the terms "interacting with" or "recognizing".

Accordingly, specificity can be determined experimentally by methods known in the art and methods as described herein. Such methods comprise, but are not limited to Western Blots, ELISA-, RIA-, ECL-, IRMA-tests and peptide scans.

As mentioned above, the present invention is not limited with respect to the "targeting moiety" since the nature of the targeting moiety depends on the desired cell into which cytoplasm the "cargo" is to be delivered. The person skilled in the art is aware of "targeting moieties" or antigens which are specific for a given cell. In line with the above, specific for a cell means that a certain targeting moiety or an antigen is exclusively, or at least predominantly, present on a given (target) cell while it is not present on other cells.

Thus, in the construct according to the present invention, the targeting moiety may be an antibody, an antibody fragment, a designed ankyrin repeat protein (DARPin), a cytokine or a ligand.

A ligand in the context of the present invention may be the counterpart of a certain cell surface molecule, or structure, preferably a cell surface receptor (membrane receptor, transmembrane receptor), i.e., a specialized integral membrane protein which commonly takes part in communication between a certain cell and the outside world. Extracellular signaling molecules (i.e., the cell surface receptor's corresponding ligand which is usually a hormones, neurotransmitter, cytokine, growth factor or a cell recognition molecule) attach to the receptor, triggering changes in the function of the cell. This process is called signal transduction. The binding initiates a chemical change on the intracellular side of the membrane. In this way the receptors play a unique and important role in cellular communications and signal transduction. Many cell surface receptors are specific for a certain type of cells or a subset of cells and, accordingly, the corresponding ligand may be a suitable targeting moiety for specifically targeting a specific cell in terms of the present invention. The person skilled in the art is aware of ligands which are specific for a given cell and can select a certain ligand based on the desired cell which is to be targeted. The amino acid sequences of ligands are well known in the art and any such known sequences may be used in the context of the present invention as a targeting moiety. The skilled person is aware of numerous sources of public information on ligand sequences. For example, the NCBI database contains both protein and encoding nucleic acid sequences for a large number of ligands. It is a matter of routine for the skilled person to choose and identify an appropriate amino acid and/or nucleic acid sequence for essentially any ligand of interest and use it as a targeting moiety in line with the present invention.

A specific ligand may, e.g., be a cytokine. Cytokines are a broad and loose category of small proteins (~5-20 kDa) that are important in cell signaling. They are released by cells and affect the behavior of other cells, and sometimes the releasing cell itself. Cytokines include chemokines, interferons, interleukins, lymphokines, tumour necrosis factor but generally not hormones or growth factors. Cytokines are produced by broad range of cells, including immune cells like macrophages, B lymphocytes, T lymphocytes and mast cells, as well as endothelial cells, fibroblasts, and various stromal cells; a given cytokine may be produced by more than one type of cell. They act through corresponding cytokine receptors which are specific for a given cell, for a certain type of cells or a subset of cells and, accordingly, the corresponding cytokine may be a suitable targeting moiety for specifically targeting a specific cell in terms of the present invention in line with the above rationale. The person skilled in the art is aware of cytokines which are specific for a given cell and can select a certain cytokine based on the desired cell which is to be targeted. The amino acid sequences of cytokines are well known in the art and any such known sequences may be used in the context of the present invention as a targeting moiety. The skilled person is aware of numerous sources of public information on cytokine sequences. For example, the NCBI database contains both protein and encoding nucleic acid sequences for a large number of cytokines. It is a matter of routine for the skilled person to choose and identify an appropriate amino acid and/or nucleic acid sequence for essentially any cytokine of interest and use it as a targeting moiety in line with the present invention. Without being bound to theory, non-limiting examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); placenta growth factor (PlGF), hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β, platelet-growth factor; transforming growth factors (TGFs) such as TGF-α and TGF-β, insulin-like growth factor-I and -II; erythropoietin (EPO); osteoinductive factors; interferons such as interferon-α, -β, -γ and -λ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, kit-ligand or FLT-3, angiostatin, thrombospondin, endostatin, tumor necrosis factor (TNF, such as TNF-α) and LT. The cytokine may be IFN-α2b.

As mentioned, the targeting moiety may also be a specific antibody or antibody fragment.

The term antibody or antibody fragment is known to the person skilled in the art and is also known as an immunoglobulin (Ig), which is a large Y-shape protein produced by plasma cells that is commonly used by the immune system to identify and neutralize foreign objects such as bacteria and viruses. The antibody recognizes a unique part of the foreign target, called an antigen. Each tip of the "Y" of an antibody contains a paratope (a structure analogous to a lock) that is specific for one particular epitope on an antigen, allowing these two structures to bind together with precision. Thus, given this specificity, antibodies or antibody fragments are the most preferred targeting moieties in terms of the present invention since the skilled person can easily prepare an antibody or an antibody fragment which is highly specific to a certain structure/antigen/epitope on a given cell which is to be targeted. Antibodies are glycoproteins belonging to the immunoglobulin superfamily. Antibodies are typically made of basic structural units—each with two large heavy chains and two small light chains. It is known to the skilled person that there are several different types of antibody heavy chains, and several different kinds of antibodies, which are grouped into different isotypes based on which heavy chain they possess. Five different antibody isotypes are known in mammals, which perform different roles, and help direct the appropriate immune response for each different type of foreign object they encounter.

Though the general structure of all antibodies is very similar, a small region at the tip of the protein is extremely variable, allowing millions of antibodies with slightly different tip structures, or antigen-binding sites, to exist. This region is known as the hypervariable region. Each of these variants can bind to a different antigen. This enormous diversity of antibodies allows the immune system to recognize an equally wide variety of antigens and can be used to prepare a specific antibody or antibody fragment in terms of the present invention which is specific enough to target a desired target cell. This capability to generate possible an antibody or antibody fragment against virtually any possible (specific) structure on a cell which is to be targeted makes antibodies or antibody fragments the best choice for a targeting moiety in terms of the invention. Thus, for this reason, the targeting moiety of the present invention may be an antibody or antibody fragment for the targeted delivery of a molecule which is to be delivered into the cytoplasm of a cell.

The antibody or fragment thereof as used in the context of the present invention is not particularly limited as long as it is an antibody or an antigen-binding fragment thereof which is capable of specifically binding to or specifically recognizing or interacting with a structure on the surface of the cell which is to be targeted in line with the foregoing.

The antibody or the antigen-binding fragment thereof which is used as a targeting moiety may be a monoclonal or a polyclonal antibody.

The term "monoclonal antibody" as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modified "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method described by Kohler, Nature 256 (1975), 495.

The term "polyclonal antibody" as used herein, refers to an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

The antibody may also be a "fully-human antibody" and refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" or "murine antibody" refers to an antibody which comprises mouse/murine immunoglobulin protein sequences only. Alternatively, a "fully-human antibody" may contain rat carbohydrate chains if produced in a rat, in a rat cell, in a hybridoma derived from a rat cell. Similarly, the term "rat antibody" refers to an antibody that comprises rat immunoglobulin sequences only. Fully-human antibodies may also be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969, 108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The antibody may also be a "chimeric antibody" which refers to an antibody which comprises a variable region of the present invention fused or chimerized with an antibody region (e.g., constant region) from another, human or non-human species (e.g., mouse, horse, rabbit, dog, cow, chicken).

The term antibody also relates to recombinant human antibodies, heterologous antibodies and heterohybrid antibodies. The term "recombinant human antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The antibody may also be a "heterologous antibody" which is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The antibody may also be a "heterohybrid antibody" and refers to an antibody having light and heavy chains of different organisms' origins. For example, an antibody having a human heavy chain associated with a murine light chain is a heterohybrid antibody. Examples of heterohybrid antibodies include chimeric and humanized antibodies.

The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: Jones Nature 321 (1986), 522-525; Reichmann Nature 332 (1998), 323-327 and Presta Curr Op Struct Biol 2 (1992), 593-596.

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084).

Accordingly, in context of the present invention, the term "antibody" relates to full immunoglobulin molecules as well as to parts of such immunoglobulin molecules (i.e., "antigen-binding fragment thereof"). Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fv, Fab', Fab'-SH, F(ab')2. The term antibody also comprises but is not limited to fully-human antibodies, chimeric antibodies, humanized antibodies, CDR-grafted antibodies and antibody constructs, like single chain Fvs (scFv) or antibody-fusion proteins. Moreover, the targeting moiety may be a $F(ab')_2$, $F(ab)_2$, Fab', a Fv antibody fragment a scFv a Fab, a VH, an scFv-Fc, an sdFv, a diabody, a triabody, a tetrabody, a minibody, a tandem-scFv, a tandem-scFv-Fc, an scFv-Fc-scFv, a Fab-scFv, a $Fab_3$, an IgG-scFv, an scFv-IgG, an IgG-$V_H$ or a single domain antibody, preferably a sdAb, a $V_H$H fragment from camelids, or a $V_{NAR}$ fragment from cartilaginous fishes.

The antibody may be a full-length antibody, i.e., to a full immunoglobulin molecule which is often also referred to as complete antibody.

"Single-chain Fv" or "scFv" antibody fragments have, in the context of the invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y. (1994), 269-315.

A "Fab fragment" as used herein is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

Antibodies, antibody constructs, antibody fragments, antibody derivatives (all being Ig-derived) to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit. The term "Ig-derived domain" particularly relates to (poly) peptide constructs comprising at least one CDR. Fragments or derivatives of the recited Ig-derived domains define (poly) peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The antibody or antibody fragment as referred to herein may have specific CDRs which determine the specificity of the targeting moiety with respect to the cell which is to be targeted. The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J. Mol. Biol. 196 (1987), 901-917 or Chothia Nature 342 (1989), 877-883.

Accordingly, in the context of the present invention, the antibody molecule described herein above is selected from the group consisting of a full antibody (immunoglobulin, like an IgG1, an IgG2, an IgG2a, an IgG2b, an IgA1, an IgGA2, an IgG3, an IgG4, an IgA, an IgM, an IgD or an IgE), F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, bivalent single chain antibody, a trivalent single chain antibody and a multivalent single chain antibody.

"Humanization approaches" are well known in the art and in particular described for antibody molecules, e.g. Ig-derived molecules. The term "humanized" refers to humanized forms of non-human (e.g., murine) antibodies or fragments thereof (such as Fv, Fab, Fab', F(ab'), scFvs, or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin see, inter alia, Jones et al., Nature 321 (1986),522-525, Presta, Curr. Op. Struct. Biol. 2 (1992),593-596. Methods for humanizing non-human antibodies are well known in the art. Generally, a humanized antibody has one or more amino acids introduced into it from a source which is non-human still retain the original binding activity of the antibody. Methods for humanization of antibodies/antibody molecules are further detailed in Jones et al., Nature 321 (1986),522-525, Reichmann et al., Nature 332 (1988),323-327, and Verhoeyen et al., Science 239 (1988),1534-1536. Specific examples of humanized antibodies, e.g. antibodies directed against EpCAM, are known in the art, see e.g. (LoBuglio, Proceedings of the American Society of Clinical Oncology Abstract (1997), 1562 and Khor, Proceedings of the American Society of Clinical Oncology Abstract (1997), 847).

Accordingly, in the context of this invention, antibody molecules or antigen-binding fragments thereof, which are humanized are preferably employed as targeting moieties and can successfully be employed in pharmaceutical compositions.

The construct according to the present invention is a construct wherein the targeting moiety targets an antigen specific for cancer, an antigen specific for infectious diseases or an antigen specific for autoimmune diseases. The person skilled in the art is aware of cell surface structures, epitopes or antigens which are specific for cells that are specific for cancer, an antigen specific for infectious diseases or an antigen specific for autoimmune diseases. Accordingly, the skilled person can choose and select an appropriate targeting moiety that targets an antigen specific for cancer, an antigen specific for infectious diseases or an antigen specific for autoimmune diseases based on the desired cell which is to be targeted.

Without being bound to theory, for the targeted delivery of a molecule which is to be delivered into the cytoplasm of a cell which is characterized by an antigen which is specific for cancer, a corresponding targeting moiety can be incorporated into the construct of the invention. As an example, any known antibody, antibody fragment, a designed ankyrin repeat protein (DARPin), ligand or cytokine that is specific for an antigen for cancer may be used. As an example, any known antibody or antibody fragment thereof may be incorporated into the construct of the present invention as long as the antibody or antibody fragment is capable of targeting a cancer cell and can, therefore, e.g., be used for cancer therapy. Thus, an antibody or antibody fragment may be selected that binds to a tumor associated antigen (TAA). A variety of tumor-associated antigens are known in the art, including but not limited to carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5ac, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PIGF, complement factors C3, C3a, C3b, C5a, C5, and an oncogene product. Exemplary anti-cancer antibodies that may be utilized in the constructs of the present invention, but are not limited to, hR1 (anti-IGF-1R, U.S. Provisional Patent Application Ser. No. 61/145,896, filed Jan. 20, 2009) hPAM4 (anti-MUC1, U.S. Pat. No. 7,282,567), hA20 (anti-CD20, U.S. Pat. No. 7,251,164), hA19 (anti-CD19, U.S. Pat. No. 7,109,304), hIMMU-31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. patent application Ser. No. 10/672,278), hRS7 (anti-EGP-1, U.S. Pat. No. 7,238,785) and hMN-3 (anti-CEA, U.S. Pat. No. 7,541,440). The skilled person will realize that this list is not limiting and any other known anti-TAA antibody may be incorporated into the construct of the present invention.

In the construct according to the present invention, the targeting moiety may also be a humanized anti-EGFR antibody single chain Fv fragment (scFv). Preferably, the humanized anti-EGFR scFv antibody has the following amino acid sequence:

```
                                        (SEQ ID NO: 2)
EVQLVESGGGLVQPGGSLRLSCAASGFSLTNYGVHWVRQAPGKGLEWL

GVIWSGGNTDYNTPFTSRFTISRDNSKNTLYLQMNSLRAEDTAVYYCA
```

-continued
```
RALTYYDYEFAYWGQGTTVTVSSGGGGSGGGGSGGGGSDIQLTQSPSF

LSASVGDRVTITCRASQSIGTNIHWYQQKPGKAPKLLIKYASESISGV

PSRFSGSGSGTEFTLTISSLQPEDFATYYCQQNNNWPTTFGAGTKLEI

KR.
```

However, the humanized anti-EGFR antibody single chain Fv fragment (scFv) as used in the present invention is not particularly limited to the above specific sequence but may also be variant thereof that binds to EGFR which comprises or consists of an amino acid sequence with at least 95%, 90%, 85%, 75%, 70%, 65%, 60%, 55% or 50% sequence homology with the sequence of SEQ ID NO: 2, as long as the antibody or antigen-binding fragment has the capability binding to EGFR. As described above, the skilled person can easily generate such antibody variants and test them with methods known in the art whether a given antibody, antibody fragment or antibody single chain Fv fragment (scFv) is capable of binding EGFR. Furthermore, the antibody or antigen-binding fragment thereof or the antibody single chain Fv fragment (scFv) is a molecule that comprises an amino acid sequence having up to 0, 1, 2, 3, 4, 5, 6, 7, 8, 9, 10 or more conservative amino acid substitutions with reference to the sequences of SEQ ID NO:2.

In the construct according to the present invention, the targeting moiety may also be a humanized anti-CD22 antibody single chain Fv fragment (scFv). The sequence of the humanized anti-CD22 antibody has been described previously in U.S. Pat. No. 7,456,260 B2 (clone SGIII).

Preferably, the humanized anti-CD22 scFv (SGIII) antibody has the following amino acid sequence:

```
                                        (SEQ ID NO: 24)
EVQLVESGGGLVQPGGSLRLSCAASGFAFSIYDMSWVRQVPGKGLEWV

SYISSGGGTTYYPDTVKGRFTISRDNSRNTLDLQMNSLRVEDTAVYYC

ARHSGYGSSYGVLFAYWGGinGTLVTVSSGGGGSGGGGSGGGGSDIQM

TQSPSSLSASVGDRVTITCRASQDISNYLNWLQQKPGKAPKLLIYYTS

ILHSGVPSRFSGSGSGTEFTLTISSLQPEDFATYYCQQGNTLPVVTFG

QGTKLEIKR.
```

However, the humanized anti-CD22 antibody single chain Fv fragment (scFv) that may be used as a targeting moiety in the present invention is not particularly limited to the above specific sequence but may also be variant thereof that binds to CD22 which comprises or consists of an amino acid sequence with at least 95%, 90%, 85%, 75%, 70%, 65%, 60%, 55% or 50% sequence homology with the sequence of SEQ ID NO: 24, as long as the antibody or antigen-binding fragment has the capability binding to CD22. As described above, the skilled person can easily generate such antibody variants and test them with methods known in the art whether a given antibody, antibody fragment or antibody single chain Fv fragment (scFv) is capable of binding CD22. Furthermore, the antibody or antigen-binding fragment thereof or the antibody single chain Fv fragment (scFv) is a molecule that comprises an amino acid sequence having up to 0, 1, 2, 3, 4, 5, 6, 7, 8, 9, 10 or more conservative amino acid substitutions with reference to the sequences of SEQ ID NO:24.

In order to determine whether an amino acid sequence has a certain degree of identity to the sequence of SEQ ID NO:2 or SEQ ID NO:24, the skilled person can use means and methods well known in the art, e.g. alignments, either manually or by using computer programs known to the person skilled in the art. Such an alignment can, e.g., be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences. In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity with the nucleic acid sequences or with the amino acid sequences as described above which are capable of binding to EGFR, when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably, the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff (1989) PNAS 89:10915) uses alignments (B) of 50, expectation (E) of 10, M=5, N=4, and a comparison of both strands.

Preferably, the amino acid substitution(s) are "conservative substitution(s)" in the above SEQ ID NO:2 or SEQ ID NO:24 which refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein as already outlined in detail above.

Similarly, for the targeted delivery of a molecule which is to be delivered into the cytoplasm of a cell which is characterized by an antigen which is specific for infectious diseases or for autoimmune diseases, a corresponding targeting moiety can be incorporated into the construct of the invention. As an example, any known antibody, antibody fragment, a designed ankyrin repeat protein (DARPin), ligand or cytokine that is specific for an antigen for infectious diseases or for autoimmune diseases may be used. The person skilled in the art is aware of cell surface structures, epitopes or antigens which are specific for cells that are specific for infectious diseases or for autoimmune diseases.

Without being bound to theory, for the targeted delivery of a molecule which is to be delivered into the cytoplasm of a cell which is characterized by an antigen which is specific for autoimmune diseases, a corresponding targeting moiety can be incorporated into the construct of the invention. As an example, any known antibody, antibody fragment, a designed ankyrin repeat protein (DARPin), ligand or cytokine that is specific for an antigen for an autoimmune disease may be used. As an example, any known antibody or antibody fragment thereof may be incorporated into the construct of the present invention as long as the antibody or antibody fragment is capable of targeting a cell affected by an autoimmune disease and can, therefore, e.g., be used for the therapy of an autoimmune disease. Thus, an antibody or antibody fragment may be selected that binds to, e.g., antigens specific for autoimmune diseases. Known antigens specific for autoimmune diseases are AMPA-GluR3, NMDA-NR1, NMDA-NR2A/B, mGluR1, mGluR5, Dsg1, Dsg3, Dsc, CD40, CD40L, CD19, CD32b, CD20, CD22, CD6, or CD74.

Similarly, for the targeted delivery of a molecule which is to be delivered into the cytoplasm of a cell which is characterized by an antigen which is specific for infectious diseases, a corresponding targeting moiety can be incorporated into the construct of the invention. As an example, any known antibody, antibody fragment, a designed ankyrin repeat protein (DARPin), ligand or cytokine that is specific for an antigen for an infectious disease may be used. As an example, any known antibody or antibody fragment thereof may be incorporated into the construct of the present invention as long as the antibody or antibody fragment is capable of targeting an infected cell and can, therefore, e.g., be used for the therapy of an infectious disease. Thus, an antibody or antibody fragment may be selected that binds to, e.g., antigens specific for infectious diseases. In infectious diseases any viral surface protein known to the person skilled in the art could be a target antigen.

The third main module of the construct of the present invention is (c) a molecule which is to be delivered into the cytoplasm of a cell (i.e., a "cargo"). The "cargo", i.e., the molecule which is to be delivered into the cytoplasm of a cell may be considered to be an "effector moiety" which exerts a desired function in the cell. The nature of the "cargo" largely depends on the question which effect is intended to be achieved by specifically delivering a respective molecule to the cytoplasm and is, therefore, not limited. Basically any molecule may be used as an effector or "cargo" as long as it has a function/functional activity that is to be delivered into the cytoplasm of a cell.

Thus, the construct according to the present invention may be a construct, wherein the molecule which is to be delivered into the cytoplasm (i.e., the "cargo") is selected from the group consisting of a therapeutic moiety, a detectable moiety, a nucleic acid molecule, preferably an siRNA, a carrier molecule, preferably a nanoparticle, a liposome and a viral vector. This "cargo" which is to be delivered into the cytoplasm is conjugated to the above modules (a) and (b) either in a chemical coupling in a covalent linkage as described above and further below or fused to the above modules (a) and (b) in the form of a fusion protein as described above and further below by recombinant methodology.

The terms therapeutic moiety (or a therapeutic agent), detectable moiety, nucleic acid molecule, siRNA, carrier molecule, nanoparticle, liposome and viral vector are known to the person skilled in the art and the nature of these "cargos" is not particularly limited in the context of the present invention. The nature of these "cargos" largely depends on the question which effect is intended to be achieved by specifically delivering a respective molecule to the cytoplasm.

If it is, e.g., desired to exert in a cell to be targeted a pharmacological reaction known to a specific compound the person skilled in the art is easily in a position to select the corresponding therapeutic moiety or therapeutic agent. Further below, non-limiting examples of therapeutic agents or therapeutic moieties are given. In general, a "therapeutic agent" or a "therapeutic moiety" is an atom, molecule, or compound that is useful in the treatment of a disease. Examples of therapeutic agents include, but are not limited to, antibodies, antibody fragments, peptides, drugs, toxins, enzymes, nucleases, hormones, immunomodulators, antisense oligonucleotides, small interfering RNA (siRNA), chelators, boron compounds, photoactive agents, dyes, and radioisotopes. In various embodiments, therapeutic moieties/agents such as cytotoxic agents, anti-angiogenic agents, pro-apoptotic agents, antibiotics, hormones, hormone antagonists, chemokines, drugs, prodrugs, toxins, enzymes or other agents may be used as adjunct therapies to the interferon-antibody DNL™ constructs described herein. Drugs of use may, e.g., possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, clofarabine, cytosine arabinoside, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, tyrosine kinase and Bruton kinase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicamycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids. Tyrosine kinase inhibitors of use may include LFM-A13, dasatinib, imatinib or nilotinib.

As will be outlined in more detail below, toxins of use may, e.g., include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10. In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use. Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA as described further below.

The therapeutic agent or moiety may also be a radionuclide.

The term "therapeutic moiety/agent" may also be understood in an even broader sense and include "diagnostic agents/moieties". A diagnostic agent or moiety is an atom, molecule, or compound that is useful in diagnosing a disease. Useful diagnostic agents or moieties include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI). Diagnostic agents or moieties are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as 110In, 111In, 177Lu, 18F, 19F, 52Fe, 62Cu, 64Cu, 67Cu, 67Ga, 68Ga, 86Y, 90Y, 89Zr, 94mTc, 94Tc, 99mTc, 120I, 123I, 124I, 125I, 131I, 154-158Gd, 32P, 11C, 13N, 15O, 186Re, 188Re, 51Mn, 52mMn, 55Co, 72As, 75Br, 76Br, 82mRb, 83Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

As will exemplarily be outlined in more detail below, the molecule which is to be delivered into the cytoplasm of a cell which is part of the construct according to the present invention may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

A detectable moiety is to be understood as a chemical moiety which is either visually detectable or in the non-visual range of the light. "Visually detectable moiety" means that the moiety or dye can be detected in the visual range of the dye simply by the eye of an individual. This includes fluorescently detectable dyes which can also be detected by the eye of the person skilled in the art upon the emission of light of a specific wavelength by the fluorescently detectable dye that has absorbed light of a certain wavelength. Thus, in the context of the present invention, the detectable moiety or dye may, e.g., be a fluorescently detectable moiety. The detectable moiety may, however, also be detectable in the non-visual range of the light. In this respect, as an example, radioactive moieties may be used.

Visually detectable moieties and non-visually detectable moieties are known to the person skilled in the art and are commonly applied in the biological field, e.g., in the detecting or localizing of specific cells. The person skilled in the art is aware of many applications for such detectable moieties. Without being bound by theory, fluorescently detectable moieties are preferred and widely known in the prior art and include, e.g., EosinY (Lin F, Fan W, Wise G E. Anal Biochem. 1991 Aug. 1; 196(2):279-83) SYPRO orange/red (Steinberg T H, Jones L J, Haugland R P, Singer V L. Anal Biochem. 1996 Aug. 1; 239(2):223-37) SYPRO ruby (Berggren K, Steinberg T H, Lauber W M, Carroll J A, Lopez M F, Chernokalskaya E, Zieske L, Diwu Z, Haugland R P, Patton W F. Anal Biochem. 1999 Dec. 15; 276(2):129-43), Deep Purple/Lightning fast (Bell P J, Karuso P. J Am Chem Soc. 2003 Aug. 6; 125(31):9304-5; Mackintosh J A, Choi H Y, Bae S H, Veal D A, Bell P J, Ferrari B C, Van Dyk D D, Verrills N M, Paik Y K, Karuso P. Proteomics. 2003 Dec.; 3(12):2273-88) and Alexa Dyes (Panchuk-Voloshina N, Haugland R P, Bishop-Stewart J, Bhalgat M K, Millard P J, Mao F, Leung W Y, Haugland R P. J Histochem Cytochem. 1999 September; 47(9):1179-88.).

It may in particular be desired to deliver a nucleic acid molecule into the cytoplasm of a cell. The delivery of nucleic acid molecules has in particular gained of importance in gene therapy. In this respect, the skilled person is aware of many methods how to prepare a desired nucleic acid molecule. Preferably, the nucleic acid molecule is an siRNA molecule which can be used to specifically knockdown the expression of a specific gene by a mechanism known to the person skilled in the art as RNA interference.

Moreover, the nucleic acid molecule, preferably the siRNA (construct) may be delivered into the cytoplasm of a cell in the form of a viral vector.

The therapeutic moiety or therapeutic agent which is to be delivered as an effector or as a "cargo" into the cytoplasm of a cell may be selected from the group consisting of a cytotoxic moiety, an antibody, an antibody fragment, a drug, a chemotherapeutic agent, a small molecule, an enzyme, a hormone, an antisense oligonucleotide, siRNA, RNAi, a radionuclide, a boron compound, a photoactive agent, an anti-angiogenic agent and a pro-apoptotic agent.

Cytotoxic moieties/agents/compounds are known to the person skilled in the art and relate to substances that are toxic to cells. Cytotoxic compounds can, e.g., result in a variety of cell fates, e.g., necrosis, cell lysis and apoptosis. A drug may be a small molecule including, e.g., a chemotherapeutic agent (i.e., a chemical substance), a radionuclide (e.g., Lu-177, Y-90, In-111, I-131), toxins from plant, microorganisms, or animals (which may be a small molecule, a peptide or a protein), like, e.g., cytotoxins, cyanotoxins, hemotoxins, neurotoxins. A pro-apoptotic agent is known to induce programmed cell death. Pro-apoptotic agents are known in the art and Bax, Bak, galectin3 and BBC3 are only cited as non-limiting examples.

Enzymes which may be used as a therapeutic moiety or therapeutic agent are highly selective macromolecular biological catalysts, which act by converting substrates into different products and may, therefore, be suitable as therapeutic moieties. The nature of the enzyme to be used as a therapeutic moiety or a therapeutic agent is not limited and depends on the disease or disorder which is to be treated or prevented. Non-limiting enzymes which may be suitable as therapeutic moieties or therapeutic agents may, e.g., be Serine proteases, DNases or RNases.

Hormones which may be used as a therapeutic moiety or therapeutic agent belong to a class of signaling molecules regulating physiology and behavior, such as metabolism, growth and development, excretion, and/or digestion. Hormones may belong to one of the following classes amines (e.g. norepinephrine), peptides (e.g., oxytocin), proteins (e.g., human growth hormone), steroids (e.g., testosterone). The nature of the hormone which may be used as a therapeutic moiety or a therapeutic agent is not limited and depends on the disease or disorder which is to be treated or prevented.

The "cargo" or effector moiety may also be an immunomodulator. An immunomodulator is an agent that when present, alters, suppresses or stimulates the body's immune system. Immunomodulators of use may include a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferon-$\alpha$, interferon-$\beta$, interferon-$\gamma$ or interferon-$\lambda$, and stem cell growth factor, such as that designated "S1 factor".

Thus, the molecule which is to be delivered into the cytoplasm of a cell may be a cytokine, such as a lymphokine, monokine, growth factor and a traditional polypeptide hormone. Cytokines have already been defined above in the context of the "targeting moiety". Yet, given the fact that cytokines may also be employed as "cargos" or "effectors" in terms of the present invention once delivered into the cytoplasm of a cell since they have the ability of immunomodulators as mentioned above, the same applies, mutatis mutandis, to the cytokines in the context of "cargos" and "effectors" as it has been set forth above with respect to cytokines in the context of the "targeting moiety". The amino acid sequences of protein or peptide immunomodulators, such as cytokines, are well known in the art and any such known sequences may be used in the context of the present invention. The skilled person is aware of numerous sources of public information on cytokine sequence as already mentioned above. Moreover, the skilled person knows many examples of cytokines as already mentioned above in the context of cytokines as "targeting moiety".

The construct of the invention may also be a construct wherein the cytotoxic moiety is selected from the group consisting of RNase A family members, ricin, abrin, alpha toxin, saporin, DNase I, Staphylococcal enterotoxin-A, pokeweed antiviral protein, gelonin, diphtheria toxin, *Pseudomonas* exotoxin, and *Pseudomonas* endotoxin.

Cytotoxicity is the capability of a cytotoxic moiety of being toxic to cells. Toxicity is the degree to which a substance, i.e., a cytotoxic moiety in terms of the present invention, can damage a cell or an organism. Toxicity may refer to the effect on a whole organism, such as an animal, bacterium, or plant, as well as the effect on a substructure of the organism, such as a cell (cytotoxicity) or an organ. In particular, in the context of the present invention, the toxicity refers to the toxicity on a cell. In general, the cytotoxic agent or moiety may be of chemical, biological, or physical nature. Chemical toxicants include, as examples, inorganic substances such as lead, mercury, and hydrofluoric acid, and organic compounds such as methyl alcohol, most medications, and poisons from living things. Radioactive chemicals are not poisonous because of their chemical nature, but because radiations emitted by nuclei are highly energetic, and destroy cells and tissues, radioactive toxicity may also be understood as "cytotoxic" in terms of the present invention. Biological toxicants include any biomolecule which has a toxic effect. Examples are given further below. Physical toxicants are substances that, due to their physical nature, interfere with biological processes. Examples include coal dust, asbestos fibers or finely divided silicon dioxide, all of which can ultimately be fatal if delivered to the organism or into a cell.

Cytotoxicity can be measured by methods known to the person skilled in the art by its effects on the target (organism, organ, tissue or, preferably, directly to the cell).

Toxins or cytotoxic moieties are well-known to the skilled person and the skilled person is aware of numerous sources of public information on these cytotoxic moieties. Moreover, the skilled person knows many examples for these cytotoxic moieties and can easily select a cytotoxic moiety.

As already mentioned above, members of the ribonuclease A (RNase A) superfamily have emerged as a potential new class of effector compounds for antibody-targeted therapy of cancer (Newton et al., 2001; De Lorenzo et al., 2004; Arndt et al., 2005; Chang et al., 2010; Liu et al., 2014). Accordingly, members of the ribonuclease A (RNase A) superfamily are, therefore, preferred "cargos" or effector moieties, i.e., molecules which are to be delivered into the cytoplasm of a cell.

RNase A family members are known from a variety of organisms and may be used as preferred "cargos" or effector moieties, i.e., molecules which are to be delivered into the cytoplasm of a cells. As examples, amphibian RNase A members may be used. Non-limiting examples of amphibian RNase A members are amphinase (derived from *Rana pipiens*) and RC-RNase (derived from *Rana catesbeiana*).

As other examples, human RNases may be used as preferred "cargos". Non-limiting examples of human RNase A members that may be used as "cargo" in accordance with the present invention are human pancreatic RNase (RNase 1 or HP-RNase; SEQ ID NO:22), eosinophil-derived neurotoxin (RNase 2), eosinophil cationic protein (RNase 3), human RNAse 4, angiogenin (RNase 5; SEQ ID NO:23), human RNAse 7 and human RNAse 8.

As another examples, bovine RNase A may be used.

All the above examples of RNases are involved in RNA metabolism/inhibition of protein synthesis and could be therapeutically used in the same way as it is described in more detail for Ranpirnase (Onconase®) herein above and below and the same applies, mutatis mutandis, to these RNases.

A preferred RNase A superfamily member is Ranpirnase (Onconase®), an RNase from the northern leopard frog *Rana pipiens*, which has been extensively studied as an antitumoral agent. It evades the human RNase inhibitor (Haigis et al., 2003) and inhibits protein synthesis by degradation of t-RNA (Saxena et al., 2002). In addition, Ranpirnase targets miRNAs and miRNA precursors being dysregulated in cancer and thus specifically interrupts key mechanisms required for malignant cell growth and tumor progression (Goparaju et al., 2011; Qiao et al., 2012). Despite its amphibian origin, Ranpirnase as a single agent has been shown to mediate no appreciable immunogenicity even when repeatedly administered to cancer patients (Mikulski et al., 1993; Mikulski et al., 2002). Previously, it has been shown that a moderate to several thousand fold increase in tumor cell killing can be achieved by targeted delivery of Ranpirnase using either chemical conjugation or genetic fusion with internalizing antibody derivatives (Newton et al., 2001; Chang et al., 2005; Krauss et al., 2005b; Liu et al., 2014). Therefore, these properties make RNase derived from Rana pipines a preferred RNase A family member in the context of the present invention. Thus, the construct according to the present invention may be a construct, wherein the RNase A family member is an RNase derived from Rana pipines.

The sequence of Ranpirnase (Onconase®) is well-known in the art and is shown in the following as SEQ ID NO:4: Q*DWLTFQKKHITNTRDVDCDNIMSTNLFHCKDKN-TFIYSRPEPVKAICKGIIASKNVL TTSEFYLSDCN-VTSRPCKYKLKKSTNKFCVTCENQAPVHFVGVGSC, wherein (*) stands for a pyroglutamate; (SEQ ID NO:4).

The present invention is not particularly limited to the above specific sequence of Ranpirnase (Onconase®). Rather, the RNase A family member may be an RNase A variant which comprises or consists of an amino acid sequence with at least 95%, 90%, 85%, 75%, 70%, 65%, 60%, 55% or 50% sequence homology with the sequence of SEQ ID NO: 4 as long as said protein or peptide having said amino acid sequence has the capability of having a cytotoxic activity comparable to the one described for Ranpirnase (Onconase®). Thus, the cytotoxic capability or activity of the variant may be similar to the activity of Ranpirnase (Onconase®) or, preferably, even higher. The person skilled in the art can prepare a corresponding variant an can easily determine whether a given variant has a correspondingly desired activity by applying methods known in the art and as, e.g., exemplified in the examples. Furthermore, the variant of the RNase A having the above desired function may have up to 0, 1, 2, 3, 4, 5, 6, 7, 8, 9, 10 or more, up to 15, 20, 30, 40 or 50 conservative amino acid substitutions with reference to the sequences of SEQ ID NO:4.

A preferred RNase A superfamily member is the human pancreatic RNase (RNase 1 or HP-RNase). Thus, the construct according to the present invention may be a construct, wherein the RNase A family member is a human pancreatic RNase (RNase 1).

The sequence of human pancreatic RNase (RNase 1) is well-known in the art and is shown in the following as SEQ ID NO:22: MALEKSLVRL LLLVLILLVL GWVQPSLGKE SRAKKFQRQH MDSDSSPSSS STYC-NQMMRR RNMTQGRCKP VNTFVHEPLV DVQN-VCFQEK VTCKNGQGNC YKSNSSMHIT DCRLTNG-SRY PNCAYRTSPK ERHIIVACEG SPYVPVHFDA SVEDST; (SEQ ID NO:22).

The present invention is not particularly limited to the above specific sequence of human pancreatic RNase (RNase 1). Rather, the RNase A family member may be an RNase A variant which comprises or consists of an amino acid sequence with at least 95%, 90%, 85%, 75%, 70%, 65%, 60%, 55% or 50% sequence homology with the sequence of SEQ ID NO: 22 as long as said protein or peptide having said amino acid sequence has the capability of having a cytotoxic activity comparable to the one described for human pancreatic RNase (RNase 1). Thus, the cytotoxic capability or activity of the variant may be similar to the activity of human pancreatic RNase (RNase 1) or, preferably, even higher. The person skilled in the art can prepare a corresponding variant an can easily determine whether a given variant has a correspondingly desired activity by applying methods known in the art and as, e.g., exemplified in the examples.

Furthermore, the variant of the RNase A having the above desired function may have up to 0, 1, 2, 3, 4, 5, 6, 7, 8, 9, 10 or more, up to 15, 20, 30, 40 or 50 conservative amino acid substitutions with reference to the sequences of SEQ ID NO:22.

A preferred RNase A superfamily member is angiogenin (RNase 5). Thus, the construct according to the present invention may be a construct, wherein the RNase A family member is angiogenin (RNase 5).

The sequence of angiogenin (RNase 5) is well-known in the art and is shown in the following as SEQ ID NO:23: MVMGLGVLLL VFVLGLGLTP PTLAQDNSRY THFLTQHYDA KPQGRDDRYC ESIMRRRGLT SPCK-DINTFI HGNKRSIKAI CENKNGNPHR ENLRISKSSF QVTTCKLHGG SPWPPCQYRA TAGFRNWVA CENGLPVHLD QSIFRRP; (SEQ ID NO:23).

The present invention is not particularly limited to the above specific sequence of angiogenin (RNase 5). Rather, the RNase A family member may be an RNase A variant which comprises or consists of an amino acid sequence with at least 95%, 90%, 85%, 75%, 70%, 65%, 60%, 55% or 50% sequence homology with the sequence of SEQ ID NO: 23 as long as said protein or peptide having said amino acid sequence has the capability of having a cytotoxic activity comparable to the one described for angiogenin (RNase 5). Thus, the cytotoxic capability or activity of the variant may be similar to the activity of angiogenin (RNase 5) or, preferably, even higher. The person skilled in the art can prepare a corresponding variant an can easily determine whether a given variant has a correspondingly desired activity by applying methods known in the art and as, e.g., exemplified in the examples. Furthermore, the variant of the RNase A having the above desired function may have up to 0, 1, 2, 3, 4, 5, 6, 7, 8, 9, 10 or more, up to 15, 20, 30, 40 or 50 conservative amino acid substitutions with reference to the sequences of SEQ ID NO:23.

The invention relates to all combinations of the above-defined (a) targeting moieties, (b) fusogenic moieties consisting of one or more fusogenic sequence(s) derived from dengue virus glycoprotein E comprising the sequence DRG-WGNGCGLFGKGGI (SEQ ID NO:1) or a sequence which shows 1 to 8 substitutions, deletions, or insertions in comparison to SEQ ID NO:1; and/or (c) "cargos", i.e., molecules which are to be delivered into the cytoplasm of a cell.

Specifically preferred constructs to which the present invention relates are the following:

The present invention relates to a construct comprising (a) a humanized anti-EGFR antibody single chain Fv fragment (scFv) as the targeting moiety; (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) an RNase derived from Rana pipines as the molecule which is to be delivered into the cytoplasm of a cell.

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLT-NYGVHWVRQAPGKGLEWLGVIWSG GNTDYNTP-FTSRFTISRDNSKNTLYLQMNSLRAEDTAVYY-CARALTYYDYEFAYWG QGTTVTVSSGGGGSGGGGSGGGGSDIQLTQSPSFL-SASVGDRVTITCRASQSIGT NIHWYQQKPGKAPKL-LIKYASESISGVPSRFSGSGSGTEFTLTISSLQPEDFA-TYYC QQNNNWPTTFGAGTKLEIKR (SEQ ID NO:2); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) an RNase derived from Rana pipines as the molecule which is to be delivered into the cytoplasm of a cell.

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLT-NYGVHWVRQAPGKGLEWLGVIWSG GNTDYNTP-FTSRFTISRDNSKNTLYLQMNSLRAEDTAVYY-CARALTYYDYEFAYWG QGTTVTVSSGGGGSGGGGSGGGGSDIQLTQSPSFL-SASVGDRVTITCRASQSIGT NIHWYQQKPGKAPKL-LIKYASESISGVPSRFSGSGSGTEFTLTISSLQPEDFA-TYYC QQNNNWPTTFGAGTKLEIKR (SEQ ID NO:2); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) an RNase derived from Rana pipines as the molecule which is to be delivered into the cytoplasm of a cell, wherein said RNase derived from Rana pipines is Ranpirnase (Onconase®) having the following amino acid sequence SEQ ID NO:4:
Q*DWLTFQKKHITNTRDVDCDNIMSTNLFHCKDK-NTFIYSRPEPVKAICKGIIASKNVL TTSEFYLSDCN-VTSRPCKYKLKKSTNKFCVTCENQAPVHFVGVGSC, wherein (*) stands for a pyroglutamate; (SEQ ID NO:4).

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLT-NYGVHWVRQAPGKGLEWLGVIWSG GNTDYNTP-FTSRFTISRDNSKNTLYLQMNSLRAEDTAVYY-CARALTYYDYEFAYWG QGTTVTVSSGGGGSGGGGSGGGGSDIQLTQSPSFL-SASVGDRVTITCRASQSIGT NIHWYQQKPGKAPKL-LIKYASESISGVPSRFSGSGSGTEFTLTISSLQPEDFA-TYYC QQNNNWPTTFGAGTKLEIKR (SEQ ID NO:2); (b) a fusogenic moiety consisting of one or more fusogenic sequence(s) selected from the group consisting of DRG-WGNGCGLFGKGGI (SEQ ID NO:1), MVDRG-WGNGCGLFGKGGIV (SEQ ID NO:3), DRG-WGNGCGLFGKGSI (SEQ ID NO:5); DRGWGNGCGLFGKGSL (SEQ ID NO:6); DRG-WGNGCGLFGKGGV (SEQ ID NO:7); DRG-WHNGCGLFGKGSI (SEQ ID NO:8); DRGWHNGCGFF-GKGSI (SEQ ID NO:9); DRGWGNGCGLFGKGSM (SEQ ID NO:10), DRGWGNGCGLFGKGSY (SEQ ID NO:11); DRGWNNGCGLFGKGSL (SEQ ID NO:12); NRG-WNNGCGLFGKGDI (SEQ ID NO:13); DRGWGN-HCGLFGKGSI (SEQ ID NO:14); DRGWGNNCGLFGK-GSI (SEQ ID NO:15); DRGWGNGCALFGKGSI (SEQ ID NO:16); DRGWGNHCGFFGKGSI (SEQ ID NO:17); DRGWDSGCFIFGKGEV (SEQ ID NO:18); NRGWGT-GCFKWGIGFV (SEQ ID NO:19) and NRGWGT-GCFEWGLGQV (SEQ ID NO:20), or a sequence which shows 1 to 8 substitutions, deletions, or insertions in comparison to SEQ ID NO:1 and SEQ ID NOs: 5 to 20, respectively; and (c) an RNase derived from Rana pipines as the molecule which is to be delivered into the cytoplasm of a cell, wherein said RNase derived from Rana pipines is Ranpirnase (Onconase®) having the following amino acid sequence SEQ ID NO:4: Q*DWLTFQKKHITNTRDVDCDNIMSTNLFHCKDK-NTFIYSRPEPVKAICKGIIASKNVL TTSEFYLSDCN-VTSRPCKYKLKKSTNKFCVTCENQAPVHFVGVGSC, wherein (*) stands for a pyroglutamate; (SEQ ID NO:4).

The present invention also relates to a construct comprising (a) a humanized anti-CD22 antibody single chain Fv fragment (scFv) as the targeting moiety; (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) an RNase derived from Rana pipines as the molecule which is to be delivered into the cytoplasm of a cell. The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAFSIYDM-SWVRQVPGKGLEWVSYISSGG GTTYYPDTVKGR-FTISRDNSRNTLDLQMNSLRVEDTAVYYCARHS-GYGSSYGVLFA YWGGinGTLVTVSSGGGGSGGGGSGGGGS-DIQMTQSPSSLSASVGDRVTITCRAS QDISNYLN-WLQQKPGKAPKLLIYYTSILHSGVPSRFSGSGS-GTEFTLTISSLQPEDFA TYYCQQGNTLPWTFGQGTKLEIKR (SEQ ID NO:24); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) an RNase derived from Rana pipines as the molecule which is to be delivered into the cytoplasm of a cell. The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAF-SIYDMSWVRQVPGKGLEWVSYISSGG GTTYYPDT-VKGRFTISRDNSRNTLDLQMNSLRVEDTAVYYCAR-HSGYGSSYGVLFA YWGGinGTLVTVSSGGGGSGGGGSGGGGS-DIQMTQSPSSLSASVGDRVTITCRAS QDISNYLN-WLQQKPGKAPKLLIYYTSILHSGVPSRFSGSGS-GTEFTLTISSLQPEDFA TYYCQQGNTLPWTFGQGTKLEIKR (SEQ ID NO:24); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) an RNase derived from Rana pipines as the molecule which is to be delivered into the cytoplasm of a cell, wherein said RNase derived from Rana pipines is Ranpirnase (Onconase®) having the following amino acid sequence SEQ ID NO:4: Q*DWLTFQKKHITNTRDVDCDNIMSTNLFHCKDK-NTFIYSRPEPVKAICKGIIASKNVL TTSEFYLSDCN-VTSRPCKYKLKKSTNKFCVTCENQAPVHFVGVGSC, wherein (*) stands for a pyroglutamate; (SEQ ID NO:4).

The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAF-SIYDMSWVRQVPGKGLEWVSYISSGG GTTYYPDT-VKGRFTISRDNSRNTLDLQMNSLRVEDTAVYYCAR-HSGYGSSYGVLFA YWGGinGTLVTVSSGGGGSGGGGSGGGGS-DIQMTQSPSSLSASVGDRVTITCRAS QDISNYLN-WLQQKPGKAPKLLIYYTSILHSGVPSRFSGSGS-GTEFTLTISSLQPEDFA TYYCQQGNTLPWTFGQGTKLEIKR (SEQ ID NO:24); (b) a fusogenic moiety consisting of one or more fusogenic sequence(s) selected from the group consisting of DRG-WGNGCGLFGKGGI (SEQ ID NO:1), MVDRG-WGNGCGLFGKGGIV (SEQ ID NO:3), DRG-WGNGCGLFGKGSI (SEQ ID NO:5); DRGWGNGCGLFGKGSL (SEQ ID NO:6); DRG-WGNGCGLFGKGGV (SEQ ID NO:7); DRG-WHNGCGLFGKGSI (SEQ ID NO:8); DRGWHNGCGFF-GKGSI (SEQ ID NO:9); DRGWGNGCGLFGKGSM (SEQ ID NO:10), DRGWGNGCGLFGKGSY (SEQ ID NO:11); DRGWNNGCGLFGKGSL (SEQ ID NO:12); NRG-WNNGCGLFGKGDI (SEQ ID NO:13); DRGWGN-HCGLFGKGSI (SEQ ID NO:14); DRGWGNNCGLFGK-GSI (SEQ ID NO:15); DRGWGNGCALFGKGSI (SEQ ID NO:16); DRGWGNHCGFFGKGSI (SEQ ID NO:17); DRGWDSGCFIFGKGEV (SEQ ID NO:18); NRGWGT-GCFKWGIGFV (SEQ ID NO:19) and NRGWGT-GCFEWGLGQV (SEQ ID NO:20), or a sequence which shows 1 to 8 substitutions, deletions, or insertions in comparison to SEQ ID NO:1 and SEQ ID NOs: 5 to 20, respectively; and (c) an RNase derived from Rana pipines as the molecule which is to be delivered into the cytoplasm of a cell, wherein said RNase derived from Rana pipines is Ranpirnase (Onconase®) having the following amino acid sequence SEQ ID NO:4: Q*DWLTFQKKHITNTRDVDCDNIMSTNLFHCKDK-NTFIYSRPEPVKAICKGIIASKNVL TTSEFYLSDCN-VTSRPCKYKLKKSTNKFCVTCENQAPVHFVGVGSC, wherein (*) stands for a pyroglutamate; (SEQ ID NO:4).

The present invention relates to a construct comprising (a) a humanized anti-EGFR antibody single chain Fv fragment (scFv) as the targeting moiety; (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a human pancreatic RNase (RNase1 or HP-RNase) as the molecule which is to be delivered into the cytoplasm of a cell.

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLT-NYGVHWVRQAPGKGLEWLGVIWSG GNTDYNTP-FTSRFTISRDNSKNTLYLQMNSLRAEDTAVYY-CARALTYYDYEFAYWG QGTTVTVSSGGGGSGGGGSGGGGSDIQLTQSPSFL-SASVGDRVTITCRASQSIGT NIHWYQQKPGKAPKL-LIKYASESISGVPSRFSGSGSGTEFTLTISSLQPEDFA-TYYC QQNNNWPTTFGAGTKLEIKR (SEQ ID NO:2); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a human pancreatic RNase (RNase1 or HP-RNase) as the molecule which is to be delivered into the cytoplasm of a cell.

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLT-NYGVHWVRQAPGKGLEWLGVIWSG GNTDYNTP-FTSRFTISRDNSKNTLYLQMNSLRAEDTAVYY-CARALTYYDYEFAYWG QGTTVTVSSGGGGSGGGGSGGGGSDIQLTQSPSFL-SASVGDRVTITCRASQSIGT NIHWYQQKPGKAPKL-LIKYASESISGVPSRFSGSGSGTEFTLTISSLQPEDFA-TYYC QQNNNWPTTFGAGTKLEIKR (SEQ ID NO:2); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a human pancreatic RNase (RNase1 or HP-RNase) as the molecule which is to be delivered into the cytoplasm of a cell, wherein said human pancreatic RNase (RNase1 or HP-RNase) has the following amino acid sequence SEQ ID NO:22:

```
                                        (SEQ ID NO: 22)
    MALEKSLVRL LLLVLILLVL GWVQPSLGKE SRAKKFQRQH

MDSDSSPSSS STYCNQMMRR RNMTQGRCKP VNTFVHEPLV

DVQNVCFQEK VTCKNGQGNC YKSNSSMHIT DCRLTNGSRY

PNCAYRTSPK ERHIIVACEG SPYVPVHFDA SVEDST;.
```

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLT-NYGVHWVRQAPGKGLEWLGVIWSG GNTDYNTP-FTSRFTISRDNSKNTLYLQMNSLRAEDTAVYY-CARALTYYDYEFAYWG QGTTVTVSSGGGGSGGGGSGGGGSDIQLTQSPSFL-SASVGDRVTITCRASQSIGT NIHWYQQKPGKAPKL-LIKYASESISGVPSRFSGSGSGTEFTLTISSLQPEDFA-TYYC QQNNNWPTTFGAGTKLEIKR (SEQ ID NO:2); (b) a fusogenic moiety consisting of one or more fusogenic sequence(s) selected from the group consisting of DRGWGNGCGLFGKGGI (SEQ ID NO:1), MVDRG-WGNGCGLFGKGGIV (SEQ ID NO:3), DRG-WGNGCGLFGKGSI (SEQ ID NO:5); DRGWGNGCGLFGKGSL (SEQ ID NO:6); DRG-WGNGCGLFGKGGV (SEQ ID NO:7); DRG-WHNGCGLFGKGSI (SEQ ID NO:8); DRGWHNGCGFF-GKGSI (SEQ ID NO:9); DRGWGNGCGLFGKGSM (SEQ ID NO:10), DRGWGNGCGLFGKGSY (SEQ ID NO:11); DRGWNNGCGLFGKGSL (SEQ ID NO:12); NRG-WNNGCGLFGKGDI (SEQ ID NO:13); DRGWGN-HCGLFGKGSI (SEQ ID NO:14); DRGWGNNCGLFGK-GSI (SEQ ID NO:15); DRGWGNGCALFGKGSI (SEQ ID NO:16); DRGWGNHCGFFGKGSI (SEQ ID NO:17); DRGWDSGCFIFGKGEV (SEQ ID NO:18); NRGWGT-GCFKWGIGFV (SEQ ID NO:19) and NRGWGT-GCFEWGLGQV (SEQ ID NO:20), or a sequence which shows 1 to 8 substitutions, deletions, or insertions in comparison to SEQ ID NO:1 and SEQ ID NOs: 5 to 20, respectively; and (c) a human pancreatic RNase (RNase1 or HP-RNase) as the molecule which is to be delivered into the cytoplasm of a cell, wherein said human pancreatic RNase (RNase1 or HP-RNase) has the following amino acid sequence SEQ ID NO:22:

```
                                        (SEQ ID NO: 22)
    MALEKSLVRL LLLVLILLVL GWVQPSLGKE SRAKKFQRQH

MDSDSSPSSS STYCNQMMRR RNMTQGRCKP VNTFVHEPLV

DVQNVCFQEK VTCKNGQGNC YKSNSSMHIT DCRLTNGSRY

PNCAYRTSPK ERHIIVACEG SPYVPVHFDA SVEDST;.
```

The present invention also relates to a construct comprising (a) a humanized anti-CD22 antibody single chain Fv fragment (scFv) as the targeting moiety; (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a human pancreatic RNase (RNase1 or HP-RNase) as the molecule which is to be delivered into the cytoplasm of a cell.

The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAF-SIYDMSWVRQVPGKGLEWVSYISSGG GTTYYPDT-VKGRFTISRDNSRNTLDLQMNSLRVEDTAVYYCAR-HSGYGSSYGVLFA YWGGinGTLVTVSSGGGGSGGGGSGGGGS-DIQMTQSPSSLSASVGDRVTITCRAS QDISNYLN-WLQQKPGKAPKLLIYYTSILHSGVPSRFSGSGS-GTEFTLTISSLQPEDFA TYYCQQGNTLPWTFGQGTKLEIKR (SEQ ID NO:24); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a human pancreatic RNase (RNase1 or HP-RNase) as the molecule which is to be delivered into the cytoplasm of a cell.

The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAFSIYDMSWVRQVPGKGLEWVSYISSGG GTTYYPDTVKGRFTISRDNSRNTLDLQMNSLRVEDTAVYYCARHSGYGSSYGVLFA YWGGinGTLVTVSSGGGGSGGGGSGGGGS-DIQMTQSPSSLSASVGDRVTITCRAS QDISNYLNWLQQKPGKAPKLLIYYTSILHSGVPSRFSGSGS-GTEFTLTISSLQPEDFA TYYCQQGNTLPWTFGQGTKLEIKR (SEQ ID NO:24); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) a human pancreatic RNase (RNase1 or HP-RNase) as the molecule which is to be delivered into the cytoplasm of a cell, wherein said human pancreatic RNase (RNase1 or HP-RNase) has the following amino acid sequence SEQ ID NO:22:

```
                                        (SEQ ID NO: 22)
MALEKSLVRL LLLVLILLVL GWVQPSLGKE SRAKKFQRQH

MDSDSSPSSS STYCNQMMRR RNMTQGRCKP VNTFVHEPLV

DVQNVCFQEK VTCKNGQGNC YKSNSSMHIT DCRLTNGSRY

PNCAYRTSPK ERHIIVACEG SPYVPVHFDA SVEDST; .
```

The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAFSIYDMSWVRQVPGKGLEWVSYISSGG GTTYYPDTVKGRFTISRDNSRNTLDLQMNSLRVEDTAVYYCARHSGYGSSYGVLFA YWGGinGTLVTVSSGGGGSGGGGSGGGGS-DIQMTQSPSSLSASVGDRVTITCRAS QDISNYLNWLQQKPGKAPKLLIYYTSILHSGVPSRFSGSGS-GTEFTLTISSLQPEDFA TYYCQQGNTLPWTFGQGTKLEIKR (SEQ ID NO:24); (b) a fusogenic moiety consisting of one or more fusogenic sequence(s) selected from the group consisting of DRGWGNGCGLFGKGGI (SEQ ID NO:1), MVDRGWGNGCGLFGKGGIV (SEQ ID NO:3), DRGWGNGCGLFGKGSI (SEQ ID NO:5); DRGWGNGCGLFGKGSL (SEQ ID NO:6); DRGWGNGCGLFGKGGV (SEQ ID NO:7); DRGWHNGCGLFGKGSI (SEQ ID NO:8); DRGWHNGCGFFGKGSI (SEQ ID NO:9); DRGWGNGCGLFGKGSM (SEQ ID NO:10), DRGWGNGCGLFGKGSY (SEQ ID NO:11); DRGWNNGCGLFGKGSL (SEQ ID NO:12); NRGWNNGCGLFGKGDI (SEQ ID NO:13); DRGWGNHCGLFGKGSI (SEQ ID NO:14); DRGWGNNCGLFGKGSI (SEQ ID NO:15); DRGWGNGCALFGKGSI (SEQ ID NO:16); DRGWGNHCGFFGKGSI (SEQ ID NO:17); DRGWDSGCFIFGKGEV (SEQ ID NO:18); NRGWGTGCFKWGIGFV (SEQ ID NO:19) and NRGWGTGCFEWGLGQV (SEQ ID NO:20), or a sequence which shows 1 to 8 substitutions, deletions, or insertions in comparison to SEQ ID NO:1 and SEQ ID NOs: 5 to 20, respectively; and (c) a human pancreatic RNase (RNase1 or HP-RNase) as the molecule which is to be delivered into the cytoplasm of a cell, wherein said human pancreatic RNase (RNase1 or HP-RNase) has the following amino acid sequence SEQ ID NO:22:

```
                                        (SEQ ID NO: 22)
MALEKSLVRL LLLVLILLVL GWVQPSLGKE SRAKKFQRQH

MDSDSSPSSS STYCNQMMRR RNMTQGRCKP VNTFVHEPLV

DVQNVCFQEK VTCKNGQGNC YKSNSSMHIT DCRLTNGSRY

PNCAYRTSPK ERHIIVACEG SPYVPVHFDA SVEDST; .
```

The present invention relates to a construct comprising (a) a humanized anti-EGFR antibody single chain Fv fragment (scFv) as the targeting moiety; (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) angiogenin (RNase 5) as the molecule which is to be delivered into the cytoplasm of a cell.

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLTNYGVHWVRQAPGKGLEWLGVIWSG GNTDYNTPFTSRFTISRDNSKNTLYLQMNSLRAEDTAVYY-CARALTYYDYEFAYWG QGTTVTVSSGGGGSGGGGSGGGGSDIQLTQSPSFLSASVGDRVTITCRASQSIGT NIHWYQQKPGKAPKLLIKYASESISGVPSRFSGSGSGTEFTLTISSLQPEDFATYYC QQNNNWPTTFGAGTKLEIKR (SEQ ID NO:2); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) angiogenin (RNase 5) as the molecule which is to be delivered into the cytoplasm of a cell.

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLTNYGVHWVRQAPGKGLEWLGVIWSG GNTDYNTPFTSRFTISRDNSKNTLYLQMNSLRAEDTAVYY-CARALTYYDYEFAYWG QGTTVTVSSGGGGSGGGGSGGGGSDIQLTQSPSFLSASVGDRVTITCRASQSIGT NIHWYQQKPGKAPKLLIKYASESISGVPSRFSGSGSGTEFTLTISSLQPEDFATYYC QQNNNWPTTFGAGTKLEIKR (SEQ ID NO:2); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) angiogenin (RNase 5) as the molecule which is to be delivered into the cytoplasm of a cell, wherein said angiogenin (RNase 5) has the following amino acid sequence SEQ ID NO:23:

```
                                             (SEQ ID NO: 23)
MVMGLGVLLL VFVLGLGLTP PTLAQDNSRY THFLTQHYDA

KPQGRDDRYC ESIMRRRGLT SPCKDINTFI HGNKRSIKAI

CENKNGNPHR ENLRISKSSF QVTTCKLHGG SPWPPCQYRA

TAGFRNVVVA CENGLPVHLD QSIFRRP;.
```

The present invention also relates to a construct comprising (a) a humanized anti-EGFR antibody single chain Fv fragment (scFv) as the targeting moiety wherein the humanized anti-EGFR scFv antibody has the following amino acid sequence: EVQLVESGGGLVQPGGSLRLSCAASGFSLTNYGVHWVRQAPGKGLEWLGVIWSG GNTDYNTPFTSRFTISRDNSKNTLYLQMNSLRAEDTAVYYCARALTYYDYEFAYWG QGTTVTVSSGGGGSGGGGSGGGGSDIQLTQSPSFLSASVGDRVTITCRASQSIGT NIHWYQQKPGKAPKLLIKYASESISGVPSRFSGSGSGTEFTLTISSLQPEDFATYYC QQNNNWPTTFGAGTKLEIKR (SEQ ID NO:2); (b) a fusogenic moiety consisting of one or more fusogenic sequence(s) selected from the group consisting of DRGWGNGCGLFGKGGI (SEQ ID NO:1), MVDRGWGNGCGLFGKGGIV (SEQ ID NO:3), DRGWGNGCGLFGKGSI (SEQ ID NO:5); DRGWGNGCGLFGKGSL (SEQ ID NO:6); DRGWGNGCGLFGKGGV (SEQ ID NO:7); DRGWHNGCGLFGKGSI (SEQ ID NO:8); DRGWHNGCGFFGKGSI (SEQ ID NO:9); DRGWGNGCGLFGKGSM (SEQ ID NO:10), DRGWGNGCGLFGKGSY (SEQ ID NO:11); DRGWNNGCGLFGKGSL (SEQ ID NO:12); NRGWNNGCGLFGKGDI (SEQ ID NO:13); DRGWGNHCGLFGKGSI (SEQ ID NO:14); DRGWGNNCGLFGKGSI (SEQ ID NO:15); DRGWGNGCALFGKGSI (SEQ ID NO:16); DRGWGNHCGFFGKGSI (SEQ ID NO:17); DRGWDSGCFIFGKGEV (SEQ ID NO:18); NRGWGTGCFKWGIGFV (SEQ ID NO:19) and NRGWGTGCFEWGLGQV (SEQ ID NO:20), or a sequence which shows 1 to 8 substitutions, deletions, or insertions in comparison to SEQ ID NO:1 and SEQ ID NOs: 5 to 20, respectively; and (c) angiogenin (RNase 5) as the molecule which is to be delivered into the cytoplasm of a cell, wherein said angiogenin (RNase 5) has the following amino acid sequence SEQ ID NO:23: MVMGLGVLLL VFVLGLGLTP PTLAQDNSRY THFLTQHYDA KPQGRDDRYC ESIMRRRGLT SPCKDINTFI HGNKRSIKAI CENKNGNPHR ENLRISKSSF QVTTCKLHGG SPWPPCQYRA TAGFRNVVVA CENGLPVHLD QSIFRRP; (SEQ ID NO:23).

The present invention also relates to a construct comprising (a) a humanized anti-CD22 antibody single chain Fv fragment (scFv) as the targeting moiety; (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) angiogenin (RNase 5) as the molecule which is to be delivered into the cytoplasm of a cell.

The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAFSIYDMSWVRQVPGKGLEWVSYISSGG GTTYYPDTVKGRFTISRDNSRNTLDLQMNSLRVEDTAVYYCARHSGYGSSYGVLFA YWGGinGTLVTVSSGGGGSGGGGSGGGGSDIQMTQSPSSLSASVGDRVTITCRAS QDISNYLNWLQQKPGKAPKLLIYYTSILHSGVPSRFSGSGSGTEFTLTISSLQPEDFA TYYCQQGNTLPWTFGQGTKLEIKR (SEQ ID NO:24); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) angiogenin (RNase 5) as the molecule which is to be delivered into the cytoplasm of a cell.

The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAFSIYDMSWVRQVPGKGLEWVSYISSGG GTTYYPDTVKGRFTISRDNSRNTLDLQMNSLRVEDTAVYYCARHSGYGSSYGVLFA YWGGinGTLVTVSSGGGGSGGGGSGGGGSDIQMTQSPSSLSASVGDRVTITCRAS QDISNYLNWLQQKPGKAPKLLIYYTSILHSGVPSRFSGSGSGTEFTLTISSLQPEDFA TYYCQQGNTLPWTFGQGTKLEIKR (SEQ ID NO:24); (b) a fusogenic moiety consisting of one or more fusogenic sequence(s) derived from dengue virus glycoprotein E comprising the sequence DRGWGNGCGLFGKGGI (SEQ ID NO:1) or a sequence which shows 1 to 8 substitutions, deletions, or insertions in comparison to SEQ ID NO:1; and (c) angiogenin (RNase 5) as the molecule which is to be delivered into the cytoplasm of a cell, wherein said angiogenin (RNase 5) has the following amino acid sequence SEQ ID NO:23:

```
                                             (SEQ ID NO: 23)
MVMGLGVLLL VFVLGLGLTP PTLAQDNSRY THFLTQHYDA

KPQGRDDRYC ESIMRRRGLT SPCKDINTFI HGNKRSIKAI

CENKNGNPHR ENLRISKSSF QVTTCKLHGG SPWPPCQYRA

TAGFRNVVVA CENGLPVHLD QSIFRRP;.
```

The present invention also relates to a construct comprising (a) a humanized anti-CD22 antibody single chain Fv fragment (scFv) as the targeting moiety wherein the humanized anti-CD22 scFv antibody has the following amino acid sequence: EVQLVESGGGLVQPGGSLRLSCAASGFAFSIYDMSWVRQVPGKGLEWVSYISSGG GTTYYPDTVKGRFTISRDNSRNTLDLQMNSLRVEDTAVYYCARHSGYGSSYGVLFA YWGGinGTLVTVSSGGGGSGGGGSGGGGSDIQMTQSPSSLSASVGDRVTITCRAS QDISNYLNWLQQKPGKAPKLLIYYTSILHSGVPSRFSGSGSGTEFTLTISSLQPEDFA TYYCQQGNTLPWTFGQGTKLEIKR (SEQ ID NO:24); (b) a fusogenic moiety consisting of one or more fusogenic sequence(s) selected from the group consisting of DRGWGNGCGLFGKGGI (SEQ ID NO:1), MVDRGWGNGCGLFGKGGIV (SEQ ID NO:3), DRGWGNGCGLFGKGSI (SEQ ID NO:5); DRGWGNGCGLFGKGSL (SEQ ID NO:6); DRGWGNGCGLFGKGGV (SEQ ID NO:7); DRGWHNGCGLFGKGSI (SEQ ID NO:8); DRGWHNGCGFFGKGSI (SEQ ID NO:9); DRGWGNGCGLFGKGSM (SEQ ID NO:10), DRGWGNGCGLFGKGSY (SEQ ID NO:11);

DRGWNNGCGLFGKGSL (SEQ ID NO:12); NRGWNNGCGLFGKGDI (SEQ ID NO:13); DRGWGNHCGLFGKGSI (SEQ ID NO:14); DRGWGNNCGLFGKGSI (SEQ ID NO:15); DRGWGNGCALFGKGSI (SEQ ID NO:16); DRGWGNHCGFFGKGSI (SEQ ID NO:17); DRGWDSGCFIFGKGEV (SEQ ID NO:18); NRGWGTGCFKWGIGFV (SEQ ID NO:19) and NRGWGTGCFEWGLGQV (SEQ ID NO:20), or a sequence which shows 1 to 8 substitutions, deletions, or insertions in comparison to SEQ ID NO:1 and SEQ ID NOs: 5 to 20, respectively; and (c) angiogenin (RNase 5) as the molecule which is to be delivered into the cytoplasm of a cell, wherein said angiogenin (RNase 5) has the following amino acid sequence SEQ ID NO:23:

```
                                            (SEQ ID NO: 23)
   MVMGLGVLLL VFVLGLGLTP PTLAQDNSRY THFLTQHYDA

KPQGRDDRYC ESIMRRRGLT SPCKDINTFI HGNKRSIKAI

CENKNGNPHR ENLRISKSSF QVTTCKLHGG SPWPPCQYRA

TAGFRNVVVA CENGLPVHLD QSIFRRP;.
```

As mentioned above, the construct according to the present invention comprises at least two, preferably the above three main modules, i.e., (a) the targeting moiety, (b) the fusogenic moiety consisting of one or more fusogenic sequence(s) and (c) the molecule which is to be delivered into the cytoplasm of a cell. All three main modules may individually be synthesized (either chemically or by recombinant technology), optionally purified and then chemically coupled in a covalent linkage. Thus, the construct according to the present invention may be a construct, wherein the targeting moiety, the fusogenic moiety consisting of one or more fusogenic sequence(s) and the molecule which is to be delivered into the cytoplasm of a cell are chemically coupled in a covalent linkage. Alternatively, module (a) and (b) may be a fusion protein while module (c) is chemically coupled in a covalent linkage to said fusion protein comprising module (a) and (b). In another alternative, module (a) and (c) may be a fusion protein while module (b) is chemically coupled in a covalent linkage to said fusion protein comprising module (a) and (c). In another alternative, module (b) and (c) may be a fusion protein while module (a) is chemically coupled in a covalent linkage to said fusion protein comprising module (b) and (c).

The term "chemically coupled in a covalent linkage" relates to conjugation techniques which are well-known to the skilled person. Many methods for making covalent or non-covalent conjugates with proteins or peptides (in particular with the fusogenic moiety or fusogenic sequence(s)/peptide of the present invention) are known in the art and any such known method may be utilized. Without being bound to theory, a construct according to the present invention can be prepared by using a heterobifunctional cross-linker, such as N-succinyl 3-(2-pyridyldithio)propionate (SPDP). Yu et al., Int. J. Cancer 56: 244 (1994). General techniques for such conjugation are well-known in the art; see, for example, Wong, Chemistry of Protein Conjugation and Cross-linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). Therefore, in view of the fact that methods for coupling moieties in a covalent linkage to each other, preferable to a protein/peptide (which may either be the "targeting moiety", the fusogenic moiety consisting of one or more fusogenic sequence(s) and/or the "cargo" in terms of the present invention) are well-known to the person skilled in the art the examples provided herewith are not limiting. For an overview of methods for (covalently) coupling a dye to a protein reference is made, e.g., to the review article of Brinkley M. Bioconjug Chem. 1992 January-February; 3(1): 2-13 and to the article of Lopez-Jaramillo, et al., in chapter 16 entitled "Vinyl Sulfone: A Multi-Purpose Function in Proteomics" the book Biochemistry, Genetics and Molecular Biology "Integrative Proteomics" edited by Hon-Chiu Eastwood Leung, Subject editors: Tsz-Kwong Man and Ricardo J. Flores, ISBN 978-953-51-0070-6, Published: Feb. 24, 2012.

The construct according to the present invention may not only comprise the above three main modules (a), (b) and (c). Rather, it may be desirable that between the individual modules (a) linker moiety/moieties are placed which may, e.g., facilitate the construction of the construct.

The construct of the present invention may also be a fusion protein. A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, 2nd Ed, 1989).

The present invention also relates to a nucleic acid molecule encoding the construct of the present invention in the form of a fusion protein. The nucleic acid is, for example a DNA, encoding one of the three main modules of the construct of the present invention. Alternatively, the nucleic acid, preferably a DNA, encodes all three main modules which are linked in-frame as defined above. Thus, the nucleic acid molecule may also encode one, two or all three of the main modules of the present invention. The above nucleic acid molecule of the present invention may be a natural nucleic acid molecule as well as a recombinant nucleic acid molecule. The nucleic acid molecule of the invention may, therefore, be of natural origin, synthetic or semi-synthetic. It may comprise DNA, RNA as well as PNA and it may be a hybrid thereof.

It is evident to the person skilled in the art that regulatory sequences may be added to the nucleic acid molecule of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard, Proc. Natl. Acad. Sci. USA 89 (1992), 5547-5551) and Gossen, Trends Biotech. 12 (1994), 58-62, or a dexamethasone-inducible gene expression system as described, e.g. by Crook, EMBO J. 8 (1989), 513-519.

Furthermore, said nucleic acid molecule may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In the context of the present invention said nucleic acid molecules are labeled. Methods for the detection of nucleic acids are well known in the art, e.g., Southern and Northern blotting, PCR or primer extension.

The nucleic acid molecule(s) of the invention may be a recombinantly produced chimeric nucleic acid molecule comprising any of the aforementioned nucleic acid molecules either alone or in combination. Preferably, the nucleic acid molecule of the invention is part of a vector.

The present invention therefore also relates to a vector comprising the nucleic acid molecule of the present invention. Accordingly, the present invention relates to vectors, preferably expression vectors comprising the nucleic acids of the invention.

The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

Furthermore, the vector of the present invention may, in addition to the nucleic acid sequences of the invention, comprise expression control elements, allowing proper expression of the coding regions in suitable hosts. Such control elements are known to the skilled person and may include a promoter, a splice cassette, translation initiation codon, translation and insertion site for introducing an insert into the vector. Preferably, the nucleic acid molecule of the invention is operatively linked to said expression control sequences allowing expression in eukaryotic or prokaryotic cells. Accordingly, the present invention relates to a vector comprising the nucleic acids of the invention, wherein the nucleic acid is operably linked to control sequences that are recognized by a host cell when the eukaryotic and/or prokaryotic (host) cell is transfected with the vector.

Control elements ensuring expression in eukaryotic and prokaryotic (host) cells are well known to those skilled in the art. As mentioned herein above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous Sarcoma Virus), human elongation factor 1α-promoter, the glucocorticoid-inducible MMTV-promoter Mouse Mammary Tumor Virus), metallothionein- or tetracyclin-inducible promoters, or enhancers, like CMV enhancer or SV40-enhancer. For expression in neural cells, it is envisaged that neurofilament-, PGDF-, NSE-, PrP-, or thy-1-promoters can be employed. Said promoters are known in the art and, inter alia, described in Charron, J. Biol. Chem. 270 (1995), 25739-25745. For the expression in prokaryotic cells, a multitude of promoters including, for example, the tac-lac-promoter or the trp promoter, has been described. Besides elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-vitrogene), pSPORT1 (GIBCO BRL), pX (Pagano, Science 255 (1992), 1144-1147), yeast two-hybrid vectors, such as pEG202 and dpJG4-5 (Gyuris, Cell 75 (1995), 791-803), or prokaryotic expression vectors, such as lambda gt11 or pGEX (Amersham-Pharmacia). Beside the nucleic acid molecules of the present invention, the vector may further comprise nucleic acid sequences encoding for secretion signals. Such sequences are well known to the person skilled in the art. Furthermore, depending on the expression system used leader sequences capable of directing the peptides of the invention to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the antibody molecules or fragments thereof of the invention may follow.

Furthermore, the vector of the present invention may also be an expression vector. The nucleic acid molecules and vectors of the invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention.

The present invention also relates to a host cell comprising the vector of the present invention. Thus, the present invention relates to a host transfected or transformed with the vector of the invention or a non-human host carrying the vector of the present invention, i.e. to a host cell or host which is genetically modified with a nucleic acid molecule according to the invention or with a vector comprising such a nucleic acid molecule. The term "genetically modified" means that the host cell or host comprises in addition to its natural genome a nucleic acid molecule or vector according to the invention which was introduced into the cell or host or into one of its predecessors/parents. The nucleic acid molecule or vector may be present in the genetically modified host cell or host either as an independent molecule outside the genome, preferably as a molecule which is capable of replication, or it may be stably integrated into the genome of the host cell or host. The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The host cell of the present invention may be any prokaryotic or eukaryotic cell. Suitable prokaryotic cells are those generally used for cloning like *E. coli* or *Bacillus subtilis*. Furthermore, eukaryotic cells comprise, for example, fungal or animal cells. Examples for suitable fungal cells are yeast cells, preferably those of the genus *Saccharomyces* and most preferably those of the species *Saccharomyces cerevisiae*. Suitable animal cells are, for instance, insect cells, vertebrate cells, preferably mammalian cells, such as e.g. HEK293, NSO, CHO, COS-7, MDCK, U2-OSHela, NIH3T3, MOLT-4, Jurkat, PC-12, PC-3, IMR, NT2N, Sk-n-sh, CaSki, C33A. These host cells, e.g. CHO-cells, may provide posts-translational (secondary) modifications to the antibody molecules of the invention, including leader peptide removal, folding and assembly of H and C chains, glycosylation of the molecule at correct sides and secretion of the functional molecule. Further suitable cell lines known in the art are obtainable from cell line depositories, like, e.g., the Deutsche Sammlung von Mikroorganismen and Zellkulturen GmbH (DSMZ) or the American Type Culture Collection (ATCC). In accordance with the present invention, it is furthermore envisaged that primary cells/cell cultures may function as host cells. Said cells are in particular derived from insects (like insects of the species *Drosophila* or *Blatta*) or mammals (like human, swine, mouse or rat). Said host cells may also comprise cells from and/or derived from cell lines like neuroblastoma cell lines. The above mentioned primary cells are well known in the art and comprise, inter alia, primary astrocytes, (mixed) spinal cultures or hippocampal cultures.

The present invention also relates to methods of producing the construct of the present invention by culturing a host cell harbouring an expression vector encoding the individual modules of the present invention or the fusion protein of the invention in culture medium, and recovering the construct/fusion protein from the host cell or culture medium. The present invention may also relate to a method for producing a construct of the present invention comprising the cultivation of the host cell of the present invention and recovering the construct from the culture.

Host cells, e.g., CHO cells, may provide post-translational (secondary) modification on the expressed binding compounds of the present invention. These modifications comprise, inter alia, glycosylation and phosphorylation.

Methods of recovering and/or subsequently purifying the construct of the present invention are known to the person skilled in the art.

The constructs as defined above are particularly useful in medical settings. Thus, the present invention also relates to a pharmaceutical composition comprising the construct of the present invention, the nucleic acid molecule of the present invention, the vector of the present invention or the host cell of the present invention and optionally a pharmaceutical acceptable carrier.

The term "treatment" and the like are used herein to generally mean obtaining a desired pharmacological and/or physiological effect. Accordingly, the treatment of the present invention may relates to the treatment of (acute) states of a certain disease but may also relate to the prophylactic treatment in terms of completely or partially preventing a disease or symptom thereof. Preferably, the term "treatment" is to be understood as being therapeutic in terms of partially or completely curing a disease and/or adverse effect and/or symptoms attributed to the disease. "Acute" in this respect means that the subject shows symptoms of the disease. In other words, the subject to be treated is in actual need of a treatment and the term "acute treatment" in the context of the present invention relates to the measures taken to actually treat the disease after the onset of the disease or the breakout of the disease. The treatment may also be prophylactic or preventive treatment, i.e., measures taken for disease prevention, e.g., in order to prevent the infection and/or the onset of the disease.

The pharmaceutical composition of the present invention may be administered via a large range of classes of forms of administration known to the skilled person, including but not limited to creams, foams, gels, lotions and ointments.

As mentioned, the present invention relates to a pharmaceutical composition, comprising an effective amount of the construct of the present invention in accordance with the above and at least one pharmaceutically acceptable excipient or carrier.

An excipient or carrier is an inactive substance formulated alongside the active ingredient, i.e., construct of the present invention in accordance with the above, for the purpose of bulking-up formulations that contain potent active ingredients. Excipients are often referred to as "bulking agents," "fillers," or "diluents". Bulking up allows convenient and accurate dispensation of a drug substance when producing a dosage form. They also can serve various therapeutic-enhancing purposes, such as facilitating drug absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors.

Thus, in line with the above, the pharmaceutical composition comprising an effective amount of the construct of the present invention may be in solid, liquid or gaseous form and may be, inter alia, in a form of (a) powder(s), (a) tablet(s), (a) solution(s) or (an) aerosol(s). It is preferred that said pharmaceutical composition optionally comprises a pharmaceutically acceptable carrier and/or diluent.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, i.e., in "an effective amount" which can easily be determined by the skilled person by methods known in the art. Administration of the suitable pharmaceutical composition is effected in accordance with the present invention by topical administration. The dosage regimen will be determined by the attending physician and clinical factors. As is well known in the medical arts, dosages for any one patient depends upon many factors, including the patient's or subject's size, body surface area, age, the particular compound to be administered, sex, time and route of administration, general health, and other drugs being administered concurrently. Proteinaceous pharmaceutically active matter may be present in amounts between 1-20 mg/kg body weight per dose; however, doses below or above this exemplary range are envisioned, especially considering the aforementioned factors.

Thus, preferably, the construct of the present invention is included in an effective amount. The term "effective amount" refers to an amount sufficient to induce a detectable therapeutic response in the subject to which the pharmaceutical composition is to be administered. In accordance with the above, the content of the construct of the present invention in the pharmaceutical composition is not limited as far as it is useful for treatment as described above, but preferably contains 0.0000001-10% by weight per total composition. Further, the construct described herein is preferably employed in a carrier. Generally, an appropriate amount of a pharmaceutically acceptable salt is used in the carrier to render the composition isotonic. Examples of the carrier include but are not limited to saline, Ringer's solution and dextrose solution. Preferably, acceptable excipients, carriers, or stabilisers are non-toxic at the dosages and concentrations employed, including buffers such as citrate, phosphate, and other organic acids; salt-forming counterions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable carriers and their formulations are described in greater detail in Remington's Pharmaceutical Sciences, 17th ed., 1985, Mack Publishing Co.

Progress can be monitored by periodic assessment. The construct of the present invention or the pharmaceutical composition of the invention may be in sterile aqueous or non-aqueous solutions, suspensions, and emulsions as well as creams and suppositories. Examples of non-aqueous solvents are propylene glycol, polyethylene glycol, vegetable oils such as olive oil, and organic esters such as ethyl oleate. Aqueous carriers include water, alcoholic/aqueous solutions, emulsions or suspensions, including saline and buffered media. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be, e.g., Tween, EDTA, Citrate, Sucrose as well as other agents being suitable for the intended use of the pharmaceutical composition that are well-known to the person skilled in the art.

In accordance with this invention, the term "pharmaceutical composition" relates to a composition for administration to a patient, preferably a human patient.

The pharmaceutical composition of the present invention may be for use in treating cancer, a cardiovascular disease, a viral infection, an immune dysfunction, an autoimmune disease, a neurologic disorder, an inherited metabolic disorders or a genetic disorder. Examples of cancer include head and neck cancer, breast cancer, renal cancer, bladder cancer, lung cancer, prostate cancer, bone cancer, brain cancer, cervical cancer, anal cancer, colon cancer, colorectal cancer, appendix cancer, eye cancer, gastric cancer, leukemia, lymphoma, liver cancer, skin cancer, ovarian cancer, penile cancer, pancreatic cancer, testicular cancer, thyroid cancer, vaginal cancer, vulvar cancer, endometrial cancer, cardiac cancer and sarcoma.

Examples of cardiovascular diseases include atherosclerosis, coronary heart disease, pulmonary heart disease and cardiomyopathy.

Examples of immune dysfunctions and autoimmune diseases include, but are not limited to, rheumatic diseases and asthma.

Examples of viral infections include, but are not limited to, infections with human immunodeficiency virus, herpes simplex virus, human papillomavirus as well as hepatitis B and C virus.

Examples of neurologic disorders include, but are not limited to, Parkinson's disease, multiple sclerosis, and dementia.

Examples of inherited metabolic disorders include, but are not limited to, Gaucher's disease and Phenylketonuria.

The invention also relates to a method for the treatment of as cancer, a cardiovascular disease, a viral infection, an immune dysfunction, an autoimmune disease, a neurologic disorder, an inherited metabolic disorders or a genetic disorder. As regards the preferred embodiments of the method for treatment the same applies, mutatis mutandis, as has been set forth above in the context of the construct or the pharmaceutical composition for use in treating cancer, a cardiovascular disease, a viral infection, an immune dysfunction, an autoimmune disease, a neurologic disorder, an inherited metabolic disorders or a genetic disorder as defined above.

In the present invention, the subject is in a preferred embodiment a mammal such as a dog, cat, pig, cow, sheep, horse, rodent, e.g., rat, mouse, and guinea pig, or a primate, e.g., gorilla, chimpanzee, and human. In a most preferable embodiment, the subject is a human.

The present invention also relates to a kit comprising a fusogenic moiety consisting of one or more fusogenic sequence(s) derived from dengue virus glycoprotein E comprising the sequence as shown in SEQ ID NO:1 or a sequence which shows 1 to 8 substitutions, deletions, or insertions in comparison to SEQ ID NO:1, the construct according to the invention, the nucleic acid molecule according the present invention, the vector according to the present invention or the host cell according to the present invention. As regards the preferred embodiments, the same applies, mutatis mutandis, as has been set forth above in the context of the construct, nucleic acid molecule, vector or the host cell according to the present invention. Advantageously, the kit of the present invention further comprises, optionally (a) buffer(s), storage solutions and/or remaining reagents or materials required for the conduct of the above and below uses and methods. Furthermore, parts of the kit of the invention can be packaged individually in vials or bottles or in combination in containers or multicontainer units. The kit of the present invention may be advantageously used, inter alia, for carrying out the methods of the invention, the preparation of the construct of the invention and could be employed in a variety of applications referred herein, e.g., in the uses as outlined above and below. Another component that can be included in the kit is instructions to a person using a kit for its use. The manufacture of the kits follows preferably standard procedures which are known to the person skilled in the art.

Finally, the present invention also relates to the use of a fusogenic moiety consisting of one or more fusogenic sequence(s) derived from dengue virus glycoprotein E for use in delivery of targeting moiety as defined above. Thus, the present invention may also relate to the use of a fusogenic moiety consisting of one or more fusogenic sequence(s) derived from dengue virus glycoprotein E as defined above for use in delivery of a therapeutic agent, a detectable moiety, a nucleic acid molecule, preferably an siRNA, a carrier molecule, preferably a nanoparticle, a liposome and a viral vector into the cytoplasm of a cell. As regards the preferred embodiments of the use the same applies, mutatis mutandis, as has been set forth above in the context of the construct. The present invention may also relate to the above use wherein said one or more fusogenic sequence(s) derived from dengue virus glycoprotein E comprise the sequence as shown in SEQ ID NO:1. Preferably, the present invention may relate to the above use, wherein said one or more fusogenic sequence(s) is a sequence which shows 1 to 8 substitutions, deletions, or insertions in comparison to SEQ ID NO:1. Again, as regards the preferred embodiments of these uses, the same applies, mutatis mutandis, as has been set forth above in the context of the construct.

In the present invention, the subject is in a preferred embodiment a mammal such as a dog, cat, pig, cow, sheep, horse, rodent, e.g., rat, mouse, and guinea pig, or a primate, e.g., gorilla, chimpanzee, and human. In a most preferable embodiment, the subject is a human.

FIG. 1: shows a schematic presentation of scFv (A), Ranpirnase-GS-scFv (B) and Ranpirnase-DEN-scFv (C). Ranpirnase was fused to the N-terminus of the scFv fragment either by a glycine-serine linker (B) or by a fusogenic peptide from dengue virus whose sequence is indicated (C). $V_H$ and $V_L$: variable domain of the heavy and light chain, respectively, of a humanized scFv fragment derived from Cetuximab. A C-terminal c-myc tag (c-myc) and a hexahistidine tag ($His_6$) was used for detection and purification purposes, respectively.

FIG. 2: shows an assessment of specific antitumor activity in vitro. Cell viability of EGFR-positive (A) and EGFR-negative (B) tumor cell lines was determined after 72 h of treatment with indicated concentrations of scFv, Ranpirnase, Ranpirnase-GS-scFv or Ranpirnase-DEN-scFv. Results are expressed relative to buffer-treated control cells. Data depict the mean values ±SE from one representative experiment performed in triplicates.

Figure 3:
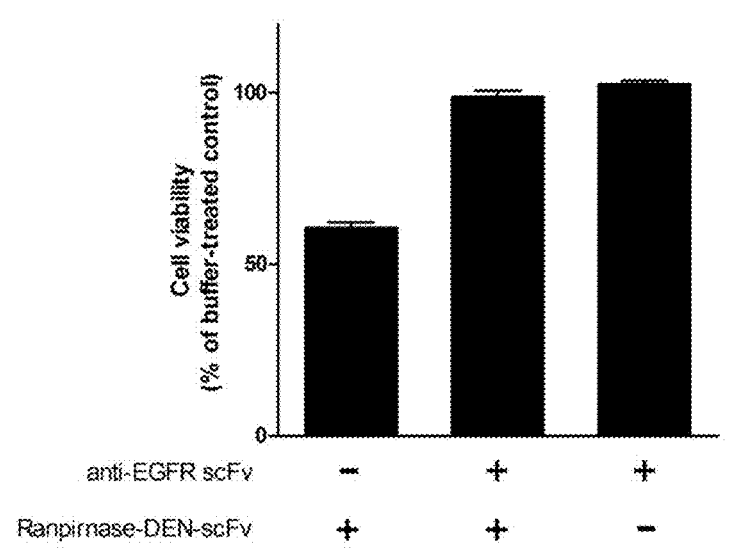

FIG. 3: shows the antigen-specific cytotoxicity of Ranpirnase-DEN-scFv. HNO211 cells were treated with Ranpirnase-DEN-scFv (20 nM) either in the presence or absence of a 50-fold molar excess of anti-EGFR scFv (1000 nM). For control, cells were treated with anti-EGFR scFv (1000 nM) alone. Cell viability was determined after 72 h by MTT-Assay. Data depict the mean values ±SE from one representative experiment performed in triplicates.

Other aspects and advantages of the invention will be described in the following examples, which are given for purposes of illustration and not by way of limitation. Each publication, patent, patent application or other document cited in this application is hereby incorporated by reference in its entirety.

EXAMPLES

Materials and Methods
1. Cloning of Ranpirnase-GS-scFv and Ranpirnase-DEN-scFv Fusion Proteins The gene of Ranpirnase (UniProtKB/Swiss-Prot: P22069.2) with an appending gene segment for a C-terminal $(G_4S)_3$ linker and flanking restriction sites was synthesized for optimized expression in mammalian cells (Entelechon, Bad Abbach, Germany) and cloned as ApaLI/PvuII fragment into the subcloning vector pMJA-1 B (Krauss et al., 2005a). For the generation of the immunoRNase Ranpirnase-GS-scFv gene, the DNA sequence of the humanized anti-epidermal growth factor receptor (EGFR) scFv IZI08 (Seifert et al., 2012) generated from the antibody C225 (Goldstein et al., 1995) was amplified by polymerase chain reaction (PCR) using ESR-1s (5'-TATAGAAGTCAGCTGGTTGAAAGC-3') (SEQ ID NO: 25) forward primer introducing a PvuII restriction site at the 5' end of the VH domain DNA sequence and ESR-2as (5'-TATAGGATCCACGTTTAATTTCCAG-3') (SEQ ID NO: 26) reverse primer that appends a BamHI restriction site at the 3' end of the VL domain DNA sequence. Prior to insertion of the IZI08 gene into the subcloning vector containing the Ranpirnase gene silent mutations for disrupting additional internal PvuII and BamHI sites were introduced. The anti-EGFR scFv IZI08 gene was subsequently cloned as PvuII/BamHI fragment downstream of the Ranpirnase gene into subcloning vector pMJA-1B containing the DNA sequences encoding for a c-myc tag and a hexahistidine tag. The DNA sequence for the standard $(G_4S)_3$ linker sequence between the RNase and antibody moiety was exchanged by the DNA sequence coding for amino acids 96-114 of glycoprotein E of dengue virus serotype 2 by overlap extension PCR resulting in Ranpirnase-DEN-scFv cassette subcloning vector pDEN14. Ranpirnase-GS-scFv and Ranpirnase-DEN-scFv fusion protein encoding genes were digested with EcoRI and cloned into mammalian cell expression vector pEE12.4 (Lonza Biologics, Slough, UK). The correct orientation of the DNA insert was confirmed by restriction digest using BamHI.

2. Cell Lines and Proteins

The cell lines A431 (human epidermoid carcinoma), MCF7 (human breast adenocarcinoma) and Raji (human Burkitt's lymphoma) were purchased from ATCC (Manassas, Va., USA). The human head and neck squamous cell carcinoma (HNSCC) cell lines HNO97 (oral cavitiy), HNO211 (oropharynx) and HNO410 (hypopharyngeal lymph node metastasis) were established from surgical specimens of HNSCC patients after informed consent and approval by the ethics committee of the Faculty of Medicine, Heidelberg University. A431, MCF7, and HNSCC cell lines were cultured in Dulbecco's modified Eagle's medium (Sigma-Aldrich, Taufkirchen, Germany) supplemented with 10% fetal bovine serum (Sigma-Aldrich), 100 U/ml penicillin and 100 µg/ml streptomycin (Sigma-Aldrich) in a humidified incubator with 5% $CO_2$ at 37° C. Raji cells were cultivated in RPMI1640 medium (Sigma-Aldrich) supplemented with 10% fetal bovine serum, 100 U/ml penicillin and 100 µg/ml streptomycin under identical conditions. HEK293-6E cells (licensed from National Research Council, Biotechnological Research Institute, Montreal, Canada) were cultured in F17 medium (Invitrogen, Life Technologies, Darmstadt, Germany) supplemented with 0.1% Kolliphor P188 (Sigma-Aldrich), 4 mM glutamine (Invitrogen) and 25 µg/ml G418 (Carl Roth, Karlsruhe, Germany) in shaker incubators at 37° C., 5% $CO_2$ and 120 rpm.

For controls Ranpimase was kindly provided by Kuslima Shogen, Alfacell Corporation.

3. Expression and Purification of scFv and ImmunoRNases

Soluble expression of the anti-EGFR scFv into the periplasm of *E. coli* TG1 cells (Stratagene, Agilent Technologies, Santa Clara, Calif., USA) using vector pAB1 (Müller et al., 2007) was performed as described previously (Diebolder et al., 2014). The scFv-containing periplasmic extract was thoroughly dialyzed against SP10 buffer (20 mM $NaH_2PO_4$, 300 mM NaCl, 10 mM imidazole, pH 8.0) at 4° C. for further purification by immobilized metal ion affinity chromatography (IMAC). RNase fusion proteins were transiently expressed in suspension growing HEK293-6E cells in shaker flasks (Falcon, Becton Dickinson, Heidelberg, Germany). At a cell density of 1.7- to 2×10⁶ cells/ml 1 µg endofree plasmid DNA and 2 µg polyethylenimine (Polysciences, Warrington, Pa., USA) per ml final culture volume were prepared separately in 1/20 of final culture volume in F17 medium without G418, mixed, incubated at room temperature for 3 min and added to HEK293-6E cells. One day after transfection, cells were supplemented with 0.5% (w/v) tryptone TN1 (Organotechnie S.A.S, La Courneuve, France). After 5 days post transfection, protein-containing supernatants were collected and dialyzed either against SP20 (20 mM $NaH_2PO_4$, 300 mM NaCl, 20 mM imidazole, pH 8.0) for Ranpimase-GS-scFv or Tris-HCl buffer (25 mM Tris, 500 mM NaCl, pH 8.2) for Ranpimase-DEN-scFv, respectively, using the SARTOFLOW® Slice 200 benchtop crossflow system (Sartorius, Goettingen, Germany). Purification of recombinant proteins by IMAC was conducted using Ni-NTA columns (GE Healthcare, Muenchen, Germany), equilibrated with the corresponding buffer. After extensive washing with buffer, bound proteins were eluted with a multiple-step gradient of imidazole containing buffer. Fractions containing the recombinant protein (determined by SDS-PAGE and Simply Blue Safe Stain (Invitrogen) and western blot) were pooled and dialyzed against PBS overnight at 4° C. Final purification and separation of monomeric scFv fragments and immunoRNases from higher molecular weight species was done by size exclusion chromatography in PBS buffer using a HiLoad 16/60 Superdex 75 prep grade column (GE Healthcare).

4. Determination of Ribonucleolytic Activity

Ribonucleolytic activity of Ranpimase and immunoRNases was measured by monitoring cleavage of the fluorogenic substrate 6-Carboxyfluorescein-dArUdGdA-Black-Hole-Quencher-1 (6-FAM-dArUdGdA-BHQ-1) (biomers.net, Ulm, Germany) over time. The fluorescence intensity was measured in 96-well black microtiter plates using an Infinite F200Pro microplate reader (Tecan, Maennedorf, Switzerland) with a 485/535 nm (excitation/emission) filter set. The reaction was carried out in 100 mM MES-NaOH buffer (pH 6.0) containing 100 mM NaCl and 6-FAM-dArUdGdA-BHQ-1 (5 nM) at 25° C. in a total reaction volume of 200 µl per well. Buffer without RNase served as negative control and an excess concentration of RNase A was used as positive control. At least three independent assays each containing triplicates were performed.

Values of $k_{cat}/K_M$ were calculated using the equation:

$$k_{cat}/K_M = \frac{(\Delta F/\Delta t)}{(F_{max} - F_{min}) \cdot [E]}$$

In this equation, $\Delta F/\Delta t$ represents the initial reaction velocity, $F_{min}$ is the initial fluroescence intensity before addition of RNase, $F_{max}$ is the fluorescence intensity after complete cleavage of the substrate by excess RNase A and [E] is the RNase concentration.

5. Antibody Binding

For determination of equilibrium-binding curves A431 cells were incubated in triplicates with serial dilutions of either purified anti-EGFR scFv, Ranpimase-GS-scFv or Ranpimase-DEN-scFv. Detection of bound antibody or immunoRNase was performed using murine anti-c-myc monoclonal antibody clone 9E10 (Roche, Penzberg, Germany) and goat-anti-mouse fluorescein isothiocyanate (FITC) conjugate (Jackson ImmunoResearch, Suffolk, UK). Fluorescence of stained cells was measured on a FACS Canto II flow cytometer (Becton Dickinson) using the FACS Diva Software (Becton Dickinson). Background fluorescence was substracted from measured median fluorescence and relative affinities were calculated by nonlinear regression using GraphPad Prism 5.0 (GraphPad Software, La Jolla, Calif., USA).

6. Cell Viability Assays and Competition Analysis

In order to assess the antitumor efficacy of the recombinant proteins, cells were seeded in a 96-well flat-bottom plate (Falcon) and incubated with different concentrations of protein or buffer as control at 37° C., 5% $CO_2$ for 72 h in a total volume of 110 µl. For adherent cell lines (A431, HNO97, HNO211, HNO410, MCF7), cell viability was determined by addition of 20 µl of a 5 mg/ml solution of 3-(4,5-dimethylthiazol-2-yl)-2,5-diphenyltetrazolium bromide (MTT) diluted in PBS. After incubation with MTT at 37° C., 5% $CO_2$ for 4 h medium was removed and cells were lysed in 100 µl lysis solution (10% SDS (w/v) and 0.6% acetic acid (v/v) in dimethyl sulfoxide) per well. Plates were incubated at room temperature for 5 min followed by gentle agitation for 5 min to dissolve released formazan crystals. Formazan concentration was determined by measuring absorbance at 570 nm (reference: 620 nm) using an Infinite F200Pro microplate reader (Tecan). For the determination of viability of the suspension cell line Raji, cells were incubated with 10 µl alamarBlue® (ThermoScientific, Rockford, Ill., USA) per well at 37° C., 5% $CO_2$ for 4 h without subsequent cell lysis. Absorbance was directly measured using the same wavelengths and instrumentation as for MTT-treated cells.

Cell viability was expressed as percentage of viable cells treated with protein related to buffer control. $IC_{50}$ was defined as the concentration at which cell viability was reduced by 50% related to buffer control. Each assay was performed at least in duplicate with each assay containing triplicates.

For competition analysis, HNO211 cells were seeded in a 96-well flat-bottom plate (Falcon) and pre-incubated for 3 h with the anti-EGFR scFv IZI08 at a concentration of 1000 nM before Ranpimase-DEN-scFv (20 nM) was added.

For controls cell were either incubated with Ranpimase-DEN-scFv (20 nM) or the anti-EGFR scFv alone (1000 nM). After incubation for 72 h at 37° C., 5% $CO_2$ cell viability was determined using the MTT assay as described above. All reactions were performed in triplicates.

Example 1

Generation of Ranpirnase-GS-scFv and Ranpirnase-DEN-scFv

For targeted killing of EGFR-expressing cancer cells, Ranpimase was fused to the N-terminus of a humanized scFv fragment with specificity identical to the clinically established mAb Cetuximab (Erbitux®) by a flexible $(G_4S)_3$ linker (Ranpimase-GS-scFv). Alternatively, Ranpimase was fused to the scFv fragment by a linker composed of a viral sequence including the putative viral fusion peptide of dengue virus serotype 2 reported to be involved in the endosomal escape mechanism of the virus (Melo et al., 2009; Zaitseva et al., 2010), resulting in the immunoRNase Ranpimase-DEN-scFv. A schematic overview of investigated proteins is shown in FIG. 1.

Example 2

Expression and Purification of scFv and ImmunoRNases

The scFv fragment was expressed in *E. coli* and isolated from the periplasmic space whereas immunoRNases Ranpimase-GS-scFv and Ranpimase-DEN-scFv were produced in HEK293-6E cells and secreted into the cell culture supernatant by employment of an $IgV_H$ leader peptide (Krauss et al., 2005a). Proteins were purified by Ni-NTA columns followed by size exclusion chromatography, yielding homogeneous protein preparations with >95% purity. Production yields after complete purification were 1.9 mg/l for scFv, 0.9 mg/l for Ranpimase-GS-scFv and 3.2 mg/l for Ranpimase-DEN-scFv, respectively.

Example 3

Functional Analysis of ImmunoRNases

Cell binding and apparent equilibrium dissociation constants ($K_D$) of scFv, Ranpimase-GS-scFv and Ranpimase-DEN-scFv were determined by flow cytometry on EGFR-expressing A431 cells. As shown in Table I both immunoRNases bound to the target antigen with high affinity similar to the scFv alone.

TABLE I

Affinity of the antibody constructs for binding to A431 cells as analyzed by flow cytometry.

|  | $K_D$ ± SE (nM) |
| --- | --- |
| scFv | 9.6 ± 1.2 |
| Ranpirnase-GS-scFv | 14.7 ± 1.2 |
| Ranpirnase-DEN-scFv | 11.2 ± 0.8 |

Ribonucleolytic activity of Ranpimase, Ranpimase-GS-scFv and Ranpimase-DEN-scFv was measured by their ability to cleave a fluorogenic RNA substrate matching the nucleobase specificity of Ranpimase (Lee and Raines, 2003). Fusion of Ranpimase to the N-terminus of the scFv fragment by a flexible glycine-serine linker slightly reduced its catalytic activity when compared to wild-type Ranpimase (Table II).

TABLE II

Ribonucleolytic activity of Ranpirnase and Ranpirnase fusion proteins

|  | $k_{cat}/K_M$ ($10^3$ M$^{-1}$s$^{-1}$)* |
| --- | --- |
| Ranpirnase | 11.3 ± 1.0 |
| Ranpirnase-GS-scFv | 8.7 ± 0.4 |
| Ranpirnase-DEN-scFv | 4.2 ± 0.4 |

*values of $k_{cat}/K_M$ (±SE) for cleavage of 6-FAM-dArUdGdA-BHQ-1 were determined as described in Material and Methods.

The catalytic activity of Ranpimase-DEN-scFv was about 2-fold lower in comparison to Ranpimase-GS-scFv, indicating that linker-dependent alterations in folding and conformation of Ranpimase or steric hindrances with substrate interaction may have occurred.

Example 4

In Vitro Cytotoxicity

For evaluating the specific toxicity towards EGFR-expressing cancer cells the scFv fragment, Ranpimase-GS-scFv, Ranpimase-DEN-scFv and Ranpimase were incubated with the EGFR-overexpressing epidermoid carcinoma cell line A431 and several EGFR-positive primary cell lines derived from resected tumors of head and neck cancer patients (HNO97, HNO211, HNO410). The EGFR-negative breast cancer cell line MCF7 and Burkitt's lymphoma cell line Raji served as negative controls. As shown in FIG. 2 and Table III the anti-EGFR scFv fragment alone had almost no effect on cell viability.

TABLE III

Antitumor activity of tested constructs towards EGFR-positive cell lines in vitro. $IC_{50}$ values are indicated as mean ± SE and are derived from at least two independent experiments each performed in triplicates.

| | $IC_{50}$ (nM) | | | |
| --- | --- | --- | --- | --- |
| | A431 | HNO97 | HNO211 | HNO410 |
| scFv | >3618 | >3618 | >3618 | >3618 |
| Ranpirnase-GS-scFv | >3618 | 1262 ± 59 | 1423 ± 712 | 2524 ± 168 |
| Ranpirnase-DEN-scFv | 38 ± 5 | 411 ± 55 | 18 ± 8 | 308 ± 85 |
| Ranpirnase | 107 ± 29 | 255 ± 38 | 4 ± 1 | 119 ± 48 |

As Ranpimase is capable to enter cells in an EGFR-independent manner (Rodriguez et al., 2007), Ranpimase alone exerted cytotoxicity towards both EGFR-negative and EGFR-positive cells (FIG. 2). Fusion of Ranpimase to the N-terminus of the scFv fragment by a flexible glycine-serine linker (Ranpimase-GS-scFv) resulted in significantly diminished cytotoxicity when compared with Ranpimase as single agent. In contrast, the immunoRNase containing the fusogenic peptide derived from dengue virus (Ranpimase-DEN-scFv) exhibited similar antitumor efficacy as Ranpimase alone towards EGFR-expressing cells yet did not affect EGFR-negative cells even at very high concentrations (FIG. 2B). Ranpimase-DEN-scFv exhibited strongest cytotoxicity towards the primary HNO211 cell line with an average $IC_{50}$ value of 18 nM corresponding to a 79-fold increase in potency compared to Ranpimase-GS-scFv.

To prove that the introduced viral linker sequence has no negative impact on the specificity of Ranpimase-DEN-scFv, we performed competition assays on the HNO211 cell line. As shown in FIG. 3 cytotoxicity of Ranpimase-DEN-scFv could be completely abrogated in the presence of a 50-fold molar excess of scFv, confirming that both compounds bind to the same targeted epitope and that the cell entry of Ranpimase-DEN-scFv is EGFR-specific and not mediated by unspecific interaction of the fusogenic peptide with the plasma membrane.

REFERENCES

Amdt, M. A., Krauss, J., Vu, B. K., Newton, D. L. and Rybak, S. M. (2005) *J. Immunother.*, 28, 245-251.

Bachran, C., Heisler, I., Fuchs, H. and Sutherland, M. (2005) *Biochem. Biophys. Res. Commun.*, 337, 602-609.

Chang, C. H., Gupta, P., Michel, R., Loo, M., Wang, Y., Cardillo, T. M. and Goldenberg, D. M. (2010) *Mol. Cancer Ther.*, 9, 2276-2286.

Chang, C. H., Sapra, P., Vanama, S. S., Hansen, H. J., Horak, I. D. and Goldenberg, D. M. (2005) *Blood*, 106, 4308-4314.

Chignola, R., Anselmi, C., Dalla Serra, M., Franceschi, A., Fracasso, G., Pasti, M., Chiesa, E., Lord, J. M., Tridente, G. and Colombatti, M. (1995) *J. Biol. Chem.*, 270, 23345-23351.

De Lorenzo, C., Arciello, A., Cozzolino, R., Palmer, D. B., Laccetti, P., Piccoli, R. and D'Alessio, G. (2004) *Cancer Res.*, 64, 4870-4874.

Diebolder, P., Keller, A., Haase, S., Schlegelmilch, A., Kiefer, J. D., Karimi, T., Weber, T., Moldenhauer, G., Kehm, R., Eis-Hubinger, A. M., et al. (2014) *MAbs*, 6, 130-142.

Erickson, H. A., Jund, M. D. and Pennell, C. A. (2006) *Protein Eng. Des. Sel.,* 19, 37-45.

Fuchs, H., Bachran, C. and Flavell, D. J. (2013) *Antibodies,* 2, 209-235.

Goldstein, N. I., Prewett, M., Zuklys, K., Rockwell, P. and Mendelsohn, J. (1995) *Clin. Cancer Res.,* 1, 1311-1318.

Goparaju, C. M., Blasberg, J. D., Volinia, S., Palatini, J., Ivanov, S., Donington, J. S., Croce, C., Carbone, M., Yang, H. and Pass, H. I. (2011) *Oncogene,* 30, 2767-2777.

Haigis, M. C., Kurten, E. L. and Raines, R. T. (2003) *Nucleic Acids Res.,* 31, 1024-1032.

Hetzel, C., Bachran, C., Fischer, R., Fuchs, H., Barth, S. and Stocker, M. (2008) *J. Immunother.,* 31, 370-376.

Huang, C. Y., Butrapet, S., Moss, K. J., Childers, T., Erb, S. M., Calvert, A. E., Silengo, S. J., Kinney, R. M., Blair, C. D. and Roehng, J. T. (2010) *Virology,* 396, 305-315.

Krauss, J., Arndt, M. A., Vu, B. K., Newton, D. L. and Rybak, S. M. (2005a) *Br. J. Haematol.,* 128, 602-609.

Krauss, J., Arndt, M. A., Vu, B. K., Newton, D. L., Seeber, S. and Rybak, S. M. (2005b) *Biochem. Biophys. Res. Commun.,* 331, 595-602.

Lee, J. E. and Raines, R. T. (2003) *Biochemistry,* 42, 11443-11450.

Liu, D., Cardillo, T. M., Wang, Y., Rossi, E. A., Goldenberg, D. M. and Chang, C. H. (2014) *Mol. Cancer,* 13, 53.

Melo, M. N., Sousa, F. J., Cameiro, F. A., Castanho, M. A., Valente, A. P., Almeida, F. C., Da Poian, A. T. and Mohana-Borges, R. (2009) *J. Mol. Biol.,* 392, 736-746.

Mikulski, S., Grossman, A., Carter, P., Shogen, K. and Costanzi, J. (1993) *Int. J. Oncol.,* 3, 57-64.

Mikulski, S. M., Costanzi, J. J., Vogelzang, N. J., McCachren, S., Taub, R. N., Chun, H., Mittelman, A., Panella, T., Puccio, C., Fine, R., et al. (2002) *J. Clin. Oncol.,* 20, 274-281.

Müller, D., Karle, A., Meissburger, B., Hofig, I., Stork, R. and Kontermann, R. E. (2007) *J. Biol. Chem.,* 282, 12650-12660.

Newton, D. L., Hansen, H. J., Mikulski, S. M., Goldenberg, D. M. and Rybak, S. M. (2001) *Blood,* 97, 528-535.

Pirie, C. M., Hackel, B. J., Rosenblum, M. G. and Wittrup, K. D. (2011) *J. Biol. Chem.,* 286, 4165-4172.

Qiao, M., Zu, L. D., He, X. H., Shen, R. L., Wang, Q. C. and Liu, M. F. (2012) *Cell Res.,* 22, 1199-1202.

Rodriguez, M., Torrent, G., Bosch, M., Rayne, F., Dubremetz, J. F., Ribo, M., Benito, A., Vilanova, M. and Beaumelle, B. (2007) *J. Cell Sci.,* 120, 1405-1411.

Saxena, S. K., Sirdeshmukh, R., Ardelt, W., Mikulski, S. M., Shogen, K. and Youle, R. J. (2002) *J. Biol. Chem.,* 277, 15142-15146.

Schulenburg, C., Ardelt, B., Ardelt, W., Arnold, U., Shogen, K., Ulbrich-Hofmann, R. and Darzynkiewicz, Z. (2007) *Cancer Biol. Ther.,* 6, 1233-1239.

Seifert, O., Plappert, A., Heidel, N., Fellermeier, S., Messerschmidt, S. K., Richter, F. and Kontermann, R. E. (2012) *Protein Eng. Des. Sel.,* 25, 603-612.

Snyder, E. L., Saenz, C. C., Denicourt, C., Meade, B. R., Cui, X. S., Kaplan, I. M. and Dowdy, S. F. (2005) *Cancer Res.,* 65, 10646-10650.

Sorkin, A. and Goh, L. K. (2009) *Exp. Cell Res.,* 315, 683-696.

Tolstikov, V. V., Cole, R., Fang, H. and Pincus, S. H. (1997) *Bioconjug. Chem.,* 8, 38-43.

Weng, A., Thakur, M., von Mallinckrodt, B., Beceren-Braun, F., Gilabert-Oriol, R., Wiesner, B., Eichhorst, J., Bottger, S., Melzig, M. F. and Fuchs, H. (2012) *J. Control. Release,* 164, 74-86.

Weyergang, A., Selbo, P. K., Berstad, M. E., Bostad, M. and Berg, K. (2011) *Lasers Surg. Med.,* 43, 721-733.

Zaitseva, E., Yang, S. T., Melikov, K., Pourmal, S. and Chemomordik, L. V. (2010) *PLoS Pathog.,* 6, e1001131.

---

The invention claimed is:

1. A construct comprising
   (a) a targeting moiety, wherein the targeting moiety is an antibody or an antibody fragment;
   (b) a fusogenic moiety consisting of one or more fusogenic sequence(s) derived from dengue virus glycoprotein E comprising the sequence DRGWGNGCGLFG-KGG 15. A pharmaceutical composition comprising the construct according to claim 1 and optionally a pharmaceutical acceptable carrier.

16. A kit comprising the fusogenic moiety of claim 1.

17. A method of delivering a therapeutic moiety, a detectable moiety, a nucleic acid molecule, preferably an siRNA, a carrier molecule, preferably a nanoparticle, a liposome and a viral vector into the cytoplasm of a cell, wherein said method comprises administering to a subject in need thereof a construct comprising the fusogenic moiety of claim 1.

18. The method according to claim 17, wherein said fusogenic moiety consists of one or more fusogenic sequence(s) derived from dengue virus glycoprotein E comprising the sequence as shown in SEQ ID NO:1.

19. The method according to claim 18, wherein said one or more fusogenic sequence(s) is a sequence which shows 1 to 4 substitutions, deletions, or insertions in comparison to SEQ ID NO:1.

* * * * *